United States Patent
Ding et al.

(10) Patent No.: US 10,287,547 B2
(45) Date of Patent: May 14, 2019

(54) ENRICHMENT AND CHARACTERIZATION OF HUMAN CORNEAL ENDOTHELIAL CELLS (HCENC) WITH NOVEL MONOCLONAL ANTIBODY

(71) Applicants: AGENCY FOR SCIENCE, TECHNOLOGY AND RESEARCH, Singapore (SG); SINGAPORE HEALTH SERVICES PTE LTD, Singapore (SG)

(72) Inventors: Mei Yee Vanessa Ding, Singapore (SG); Boon Hwa Andre Choo, Singapore (SG); Chui Ping Angela Chin, Singapore (SG); Jodhbir Singh Mehta, Singapore (SG); Gary Peh, Singapore (SG)

(73) Assignees: AGENCY FOR SCIENCE, TECHNOLOGY AND RESEARCH, Singapore (SG); SINGAPORE HEALTH SERVICES PTE LTD, Singapore (SG)

( * ) Notice: Subject to any disclaimer, the term of this patent is extended or adjusted under 35 U.S.C. 154(b) by 0 days.

(21) Appl. No.: 15/303,520

(22) PCT Filed: Apr. 11, 2014

(86) PCT No.: PCT/SG2014/000161
§ 371 (c)(1),
(2) Date: Oct. 11, 2016

(87) PCT Pub. No.: WO2015/156734
PCT Pub. Date: Oct. 15, 2015

(65) Prior Publication Data
US 2017/0037366 A1  Feb. 9, 2017

(51) Int. Cl.
| | |
|---|---|
| *C12N 5/12* | (2006.01) |
| *C12N 5/079* | (2010.01) |
| *C07K 16/28* | (2006.01) |
| *C07K 16/18* | (2006.01) |
| *C07K 16/40* | (2006.01) |

(52) U.S. Cl.
CPC ............ *C12N 5/0621* (2013.01); *C07K 16/18* (2013.01); *C07K 16/28* (2013.01); *C07K 16/2803* (2013.01); *C07K 16/40* (2013.01); *C07K 2317/33* (2013.01)

(58) Field of Classification Search
CPC ........ A61K 2039/505; A61K 2039/507; A61K 39/395; A61K 49/0058; C12N 5/12
See application file for complete search history.

(56) References Cited

FOREIGN PATENT DOCUMENTS

WO  WO-2013036754 A2 *  3/2013  ........... G01N 33/574

OTHER PUBLICATIONS

Pak et al. Expression of 1-Cys peroxiredoxin in the corneal would-healing process. Cornea. 2006;25:S29-S35.*
Paul WE. Fundamental immunology, 3rd ed. Raven Press. 1993;292-95.*
Bendig MM. Humanization of rodent monoclonal antibodies by CDR grafting. Methods: A Companion to Methods in Enzymology. 1995;8:83-93.*
Ummanni et al. Prostate cancer-associated antoantibodies in serum against tumor-associated antigens as potential new biomarkers. Journal of Proteomics. 2015;119:218-229.*
PCT Notification of Transmittal of the International Search Report and the Written Opinion of the International Searching Authority, or the Declaration for PCT Counterpart Application No. PCT/SG2014/000161, 10 pp., (dated Jul. 9, 2014).
PCT Notification Concerning Transmittal of International Preliminary Report on Patentability (Chapter I of the Patent Cooperation Treaty) for PCT Counterpart Application No. PCT/SG2014/000161, 7 pp., (dated Oct. 20, 2016).
Cyrus Chothia, et al., "Conformations of Immunoglobulin Hypervariable Regions", Nature, vol. 342, pp. 877-883, (Dec. 21-28, 1989).
Yuen Kuen Cheong, et al., "Identification of Cell Surface Markers Glypican-4 and CD200 That Differentiate Human Corneal Endothelium From Stromal Fibroblasts", Investigative Ophthalmology & Visual Science, vol. 54, No. 7, pp. 4538-4547, (Jul. 2013).
Zhenzhi Chng, et al., "High Throughput Gene Expression Analysis Identifies Reliable Expression Markers of Human Corneal Endothelial Cells", PLoS ONE, vol. 8, No. 7, e67546, pp. 1-15, (Jul. 2013).
Gary SL Peh, et al., "Optimization of Human Corneal Endothelial Cell Culture: Density Dependency of Successful Cultures In Vitro", BMC Research Notes, vol. 6, No. 176, pp. 1-9, (2013).
Gary S. L. Peh, et al., "Human Corneal Endothelial Cell Expansion for Corneal Endothelium Transplantation: An Overview", Transplantation, vol. 91, No. 8, pp. 811-819, (Apr. 27, 2011).
Vanessa M.Y. Ding, et al., "FGF-2 Modulates Wnt Signaling in Undifferentiated hESC and iPS Cells Through Activated PI3-K/GSK3β Signaling", Journal of Cellular Physiology, vol. 225, No. 2, pp. 417-428, (2010).
Andre B. Choo, et al., "Selection Against Undifferentiated Human Embryonic Stem Cells by a Cytotoxic Antibody Recognizing Podocalyxin-Like Protein-1", Stem Cells, vol. 26, No. 6, pp. 1454-1463, (2008).

(Continued)

*Primary Examiner* — Lynn Y Fan
(74) *Attorney, Agent, or Firm* — Womble Bond Dickinson (US) LLP

(57) ABSTRACT

This invention refers to an antibody or an antigen binding portion thereof, that binds specifically to human corneal endothelial cells (hCENCs), wherein the target of the monoclonal antibody, or antigen binding portion thereof, is essentially cell surface-expressed Peroxiredoxin-6 (Prdx6), as well as to methods for determining suitability of a cell sample for corneal transplantation, for quantitative enrichment of human corneal endothelial cells from a mixture of cells, and for isolating human corneal endothelial cells from a mixture of cell.

4 Claims, 17 Drawing Sheets
Specification includes a Sequence Listing.

(56) References Cited

OTHER PUBLICATIONS

Lesley Y. Chan, et al., "Normalized Median Fluorescence: An Alternative Flow Cytometry Analysis Method for Tracking Human Embryonic Stem Cell States During Differentiation", Tissue Engineering: Part C, vol. 19, No. 2, pp. 156-165, (2013).

Jhang Ho Pak, et al., "Expression of 1-Cys Peroxiredoxin in the Corneal Wound-Healing Process", Cornea, vol. 25, Supp. 1, pp. S29-S35, (Dec. 2006).

* cited by examiner (C)

Surface staining (Live)

Intracellular staining (Fix and Perm)

Universal code (SEQ ID NO:7)
Total amino acid number: 122, MW=13545
Max ORF: 1-366, 122 AA, MW=13545

```
1     CAGGTCAAACTGCAGCAGTCAGGACCTGAGCTGGTGAAGCCTGGGGCTTCAGTGAAGGTA
1      Q  V  K  L  Q  Q  S  G  P  E  L  V  K  P  G  A  S  V  K  V

61    TCCTGCAAGGCTTCTGGTTATGCATTCACTAGCTACAACATGTACTGGGTGAAGCAGAGC
21     S  C  K  A  S  G  Y  A  F  T  S  Y  N  M  Y  W  V  K  Q  S

121   CATGGAAAGAGCCTTGAGTGGATTGGATATATTGATCCTTACAATGGTGGTACTAGCTAC
41     H  G  K  S  L  E  W  I  G  Y  I  D  P  Y  N  G  G  T  S  Y

181   AACCAGAAGTTCAAGGGCAAGGCCACATTGACTGTTGACAAGTCCTCCAGCACAGCCTAC
61     N  Q  K  F  K  G  K  A  T  L  T  V  D  K  S  S  S  T  A  Y

241   ATGCATCTCAACAGCCTGACATCTGAGGACTCTGCAGTCTATTACTGTGCAAGGCCGATC
81     M  H  L  N  S  L  T  S  E  D  S  A  V  Y  Y  C  A  R  P  I

301   TATGATGGTTACTACGGCTGGTACTTCGATGTCTGGGGCCAAGGGACCACGGTCACCGTC
101    Y  D  G  Y  Y  G  W  Y  F  D  V  W  G  Q  G  T  T  V  T  V

361   TCCTCA
121    S  S
```

FIG. 8 continued (B)

Translation of A12L3 (1-321)
Universal code (SEQ ID NO:8)
Total amino acid number: 107, MW=11567
Max ORF: 1-321, 107 AA, MW=11567

```
1    GACATTGAGCTCACCCAGTCTCCAGCACTCATGTCTGCATCTCCAGGGGAGAAGGTCACC
1     D  I  E  L  T  Q  S  P  A  L  M  S  A  S  P  G  E  K  V  T

61   ATGACCTGCAGTGCCAGCTCAAGTGTAAGTTACATGTACTGGTACCAGCAGAAGCCAAGA
21    M  T  C  S  A  S  S  S  V  S  Y  M  Y  W  Y  Q  Q  K  P  R

121  TCCTCCCCCAAACCCTGGATTTATCTCACATCCAACCTGGCTTCTGGAGTCCCTGCTCGC
41    S  S  P  K  P  W  I  Y  L  T  S  N  L  A  S  G  V  P  A  R

181  TTCAGTGGCAGTGGGTCTGGGACCTCTTACTCTCTCACAATCAGCAGCATGGAGGCTGAA
61    F  S  G  S  G  S  G  T  S  Y  S  L  T  I  S  S  M  E  A  E

241  GATGCTGCCACTTATTACTGCCAGCAGTGGAGTAGTAACCCCCTCACGTTCGGTGCTGGG
81    D  A  A  T  Y  Y  C  Q  Q  W  S  S  N  P  L  T  F  G  A  G

301  ACCAAGCTGGAAATAAAACGG
101   T  K  L  E  I  K  R
```

FIG. 8 continued (C)

TAG-2A12 (CE2A12)
>CE2A12| HeavyChain
QVKLQQSGPELVKPGASVKVSCKASGYAFTSYNMYWVKQSHGKSLEWI
GYIDPYNGGTSYNQKFKG
KATLTVDKSSSTAYMHLNSLTSEDSAVYYCARPIYDGYYGWYFDVWGQG
TTVTVSS (SEQ ID NO:7)
heavy chain CDR 1: GYAFTSYNMY (SEQ ID NO:1)
heavy chain CDR 2: YIDPYNGGTSYNQKFKG (SEQ ID NO:2)
heavy chain CDR 3: PIYDGYYGWYFDV (SEQ ID NO:3)

>CE2A12|LightChain
DIELTQSPALMSASPGEKVTMTCSASSSVSYMYWYQQKPRSSPKPWIYL
TSNLAS
GVPARFSGSGSGTSYSLTISSMEAEDAATYYCQQWSSNPLTFGAGTKLEI
KR (SEQ ID NO:8)
Light chain CDR 1: SASSSVSYMY (SEQ ID NO:4)
Light chain CDR 2: LTSNLAS (SEQ ID NO:5)
Light chain CDR 3: QQWSSNPLT (SEQ ID NO:6)

FIG. 9

TAG 2A12-Peroxiredoxin6 (SEQ ID NO:9)

MPGGLLLGDVAPNFEANTTVGRIR<u>FHDFLGDSWGILFSH</u>PRDFTPVCTTELGRAAKLAPEFAKRN
VKLIALSIDSVEDHLAWSK<u>DINAYNCEEPTEK</u>LPFPIIDDRNR<u>ELAILLGMLDPAEK</u>DEKGMPVTARV
VFVFGPDKKLKLSILYPATTGRNFDEILRVVISLQLTAEKRVATPVDWKDGDSVMVLPTIPEEEAKKL
FPKGVFTKELPSGKKYLRYTPQP

| mAbs | Antigen Target | Molecular Weight (with hCENC) | Molecular Weight (with other cell lines) | Sequence homology to PRDX-6 (uniprot BlastP) | Remarks |
|---|---|---|---|---|---|
| TAG 2A12 | Prdx6 | 28kDa | >25kDa (Based on product sheet) | 100% | Based our own findings Anti-PRDX6 Abcam # ab16946 |
| TAG 1A3 | CD166/ALCAM | 80kDa | 100-105kDa (Based on product sheet) | 23% | Based our own findings Anti-CD166 Abcam #ab109215 |
| Anti-CD200 | CD200 | N.A. | 40-45kDa (Based on Product Spec Sheet) | 4% | Anti-CD200 BD Pharmagen #552023 |
| Anti-GPC4 | GPC4 | N.A. | 62.4kDa (Based on product Spec Sheet) | 29% | Anti-GPC4 Novus Biological #NBP1-45286 |
| mAb 9.3E | Unknown | 130kDa | 130kDa (human umbilical vein endothelial cells) | N.A. | K.Engelmann et. al. 2001 Exp Eye Res. 73, 9-16 |
| 2B4.14.1 | Tamm-Horsfall Glycoprotein (THGP) | N.A. | 65kDa (with purified THGP); 250-325kDa (with pig and human ciliary body glycoprotein) | No significant similarities found | Howell et. al.; 1991 Inv. Opth. & Vis Sci. 32 (9); Howell et. al. 1994 Inv. Opth. & Vis Sci. 35 (8) |
| KP14D10 | Unknown | N.A. | 60kDa (Bovine corneal endothelial cells) | N.A. | Sakamoto et. al. 1991 Graefe's Arch Clinical Exp Opth. 229:587-592 (Note: Antibody is an IgM) |

FIG. 10 continued (B)

Sequences producing significant alignments:

Select: All None Selected:0

Alignments  Download ▾  GenPept  Graphics  Distance tree of results  Multiple alignment

| Description | Max. score | Total score | Query cover | E value | Ident | Accession |
|---|---|---|---|---|---|---|
| RecName: Full=OX-2 membrane glycoprotein; AltName: CD antigen=CD200; Flags: Precursor >gi|XP_005247539.1|PREDICTED: OX-2 membra | 14.2 | 14.2 | 4% | 3.1 | 44% | P41217.4 |
| RecName: Full=Glypican-4; AltName: Full=K-glypican; Contains: RecName: Full=Secreted glypican-4; Flags: Precursor >gi|NP_001439.2|glypican | 22.3 | 39.3 | 29% | 0.017 | 29% | O75487.4 |
| RecName: Full=CD166 antigen; AltName: Full=Activated leukocyte cell adhesion molecule; AltName: CD antigen=CD166; Flags: Precursor >gi|NP | 16.9 | 30.4 | 23% | 0.81 | 24% | Q13740.2 |

SEQUENCE LISTING

```
<160> NUMBER OF SEQ ID NOS: 9

<210> SEQ ID NO 1
<211> LENGTH: 10
<212> TYPE: PRT
<213> ORGANISM: Artificial sequence
<220> FEATURE:
<223> OTHER INFORMATION: Heavy chain CDR1 of TAG-2A12 (CE2A12)

<400> SEQUENCE: 1

Gly Tyr Ala Phe Thr Ser Tyr Asn Met Tyr
1               5                   10

<210> SEQ ID NO 2
<211> LENGTH: 17
<212> TYPE: PRT
<213> ORGANISM: Artificial sequence
<220> FEATURE:
<223> OTHER INFORMATION: Heavy chain CDR2 of TAG-2A12 (CE2A12)

<400> SEQUENCE: 2

Tyr Ile Asp Pro Tyr Asn Gly Gly Thr Ser Tyr Asn Gln Lys Phe Lys
1               5                   10                  15

Gly

<210> SEQ ID NO 3
<211> LENGTH: 13
<212> TYPE: PRT
<213> ORGANISM: Artificial sequence
<220> FEATURE:
<223> OTHER INFORMATION: Heavy chain CDR3 of TAG-2A12 (CE2A12)

<400> SEQUENCE: 3

Pro Ile Tyr Asp Gly Tyr Tyr Gly Trp Tyr Phe Asp Val
```

<210> SEQ ID NO 4
<211> LENGTH: 10
<212> TYPE: PRT
<213> ORGANISM: Artificial sequence
<220> FEATURE:
<223> OTHER INFORMATION: Light chain CDR1 of TAG-2A12 (CE2A12)

<400> SEQUENCE: 4

Ser Ala Ser Ser Ser Val Ser Tyr Met Tyr
1               5                   10

<210> SEQ ID NO 5
<211> LENGTH: 7
<212> TYPE: PRT
<213> ORGANISM: Artificial sequence
<220> FEATURE:
<223> OTHER INFORMATION: Light chain CDR2 of TAG-2A12 (CE2A12)

<400> SEQUENCE: 5

Leu Thr Ser Asn Leu Ala Ser
1               5

<210> SEQ ID NO 6
<211> LENGTH: 9
<212> TYPE: PRT
<213> ORGANISM: Artificial sequence
<220> FEATURE:
<223> OTHER INFORMATION: Light chain CDR3 of TAG-2A12 (CE2A12)

<400> SEQUENCE: 6

Gln Gln Trp Ser Ser Asn Pro Leu Thr
1               5

<210> SEQ ID NO 7
<211> LENGTH: 122
<212> TYPE: PRT
<213> ORGANISM: Artificial sequence
<220> FEATURE:
<223> OTHER INFORMATION: Heavy chain TAG-2A12 (CE2A12)

<400> SEQUENCE: 7

Gln Val Lys Leu Gln Gln Ser Gly Pro Glu Leu Val Lys Pro Gly Ala
1               5                   10                  15

Ser Val Lys Val Ser Cys Lys Ala Ser Gly Tyr Ala Phe Thr Ser Tyr
                20                  25                  30

Asn Met Tyr Trp Val Lys Gln Ser His Gly Lys Ser Leu Glu Trp Ile
            35                  40                  45

Gly Tyr Ile Asp Pro Tyr Asn Gly Gly Thr Ser Tyr Asn Gln Lys Phe
        50                  55                  60

Lys Gly Lys Ala Thr Leu Thr Val Asp Lys Ser Ser Ser Thr Ala Tyr
65                  70                  75                  80

Met His Leu Asn Ser Leu Thr Ser Glu Asp Ser Ala Val Tyr Tyr Cys
                85                  90                  95

Ala Arg Pro Ile Tyr Asp Gly Tyr Tyr Gly Trp Tyr Phe Asp Val Trp
                100                 105                 110

Gly Gln Gly Thr Thr Val Thr Val Ser Ser
            115                 120

<210> SEQ ID NO 8
<211> LENGTH: 107
<212> TYPE: PRT

<213> ORGANISM: Artificial sequence
<220> FEATURE:
<223> OTHER INFORMATION: Light chain TAG-2A12 (CE2A12)

<400> SEQUENCE: 8

Asp Ile Glu Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Ile Lys Arg
            100                 105

<210> SEQ ID NO 9
<211> LENGTH: 224
<212> TYPE: PRT
<213> ORGANISM: Homo sapiens

<400> SEQUENCE: 9

Met Pro Gly Gly Leu Leu Gly Asp Val Ala Pro Asn Phe Glu Ala
1               5                   10                  15

Asn Thr Thr Val Gly Arg Ile Arg Phe His Asp Phe Leu Gly Asp Ser
            20                  25                  30

Trp Gly Ile Leu Phe Ser His Pro Arg Asp Phe Thr Pro Val Cys Thr
        35                  40                  45

Thr Glu Leu Gly Arg Ala Ala Lys Leu Ala Pro Glu Phe Ala Lys Arg
    50                  55                  60

Asn Val Lys Leu Ile Ala Leu Ser Ile Asp Ser Val Glu Asp His Leu
65                  70                  75                  80

Ala Trp Ser Lys Asp Ile Asn Ala Tyr Asn Cys Glu Glu Pro Thr Glu
                85                  90                  95

Lys Leu Pro Phe Pro Ile Ile Asp Asp Arg Asn Arg Glu Leu Ala Ile
            100                 105                 110

Leu Leu Gly Met Leu Asp Pro Ala Glu Lys Asp Glu Lys Gly Met Pro
        115                 120                 125

Val Thr Ala Arg Val Val Phe Val Phe Gly Pro Asp Lys Lys Leu Lys
    130                 135                 140

Leu Ser Ile Leu Tyr Pro Ala Thr Thr Gly Arg Asn Phe Asp Glu Ile
145                 150                 155                 160

Leu Arg Val Val Ile Ser Leu Gln Leu Thr Ala Glu Lys Arg Val Ala
                165                 170                 175

Thr Pro Val Asp Trp Lys Asp Gly Asp Ser Val Met Val Leu Pro Thr
            180                 185                 190

Ile Pro Glu Glu Glu Ala Lys Lys Leu Phe Pro Lys Gly Val Phe Thr
        195                 200                 205

Lys Glu Leu Pro Ser Gly Lys Lys Tyr Leu Arg Tyr Thr Pro Gln Pro
    210                 215                 220

ENRICHMENT AND CHARACTERIZATION OF HUMAN CORNEAL ENDOTHELIAL CELLS (HCENC) WITH NOVEL MONOCLONAL ANTIBODY

CROSS-REFERENCE TO RELATED APPLICATION

This patent application is a U.S. National Phase Application under 35 U.S.C. § 371 of International Application No. PCT/SG2014/000161, filed Apr. 11, 2014, entitled ENRICHMENT AND CHARACTERIZATION OF HUMAN CORNEAL ENDOTHELIAL CELLS (HCENC) WITH NOVEL MONOCLONAL ANTIBODY.

INCORPORATION BY REFERENCE

This patent application incorporates by reference the material (i.e., Sequence Listing) in the ASCII text file named Sequence_Listing.txt, created on Oct. 6, 2016, having a file size of 5,827 bytes.

FIELD OF THE INVENTION

The present invention relates generally to the field of molecular biology. In particular, the present invention relates to novel monoclonal antibodies for detecting human corneal endothelial cells (hCENCs).

BACKGROUND OF THE INVENTION

The human corneal endothelium is the most important monolayer of cells in the cornea. It plays a significant role in maintaining corneal transparency by regulating the leaky barriers between the aqueous humor and corneal stroma. The corneal endothelium cell layer is derived from neural crest cells during the first 16 weeks of gestation. Human corneal endothelial cells (hCENC), however, have very limited proliferative capacity in vivo and the density of hCENC in the cornea shows an inverse relationship with age. Damage to the corneal endothelium layer by accidental or surgical corneal trauma and diseases such as Fuchs' dystrophy often result in corneal edema and corneal blindness. Currently, cornea transplantation is the main treatment option for irreversible damages on the corneal endothelium. However, the success of the treatment is limited by the scarcity of transplant-grade corneas from suitable donors. Hence, fresh cadaveric corneas are often used for isolation and expansion of hCENC, which have been regarded as a potential source of cells for replacing damaged corneal endothelium.

The anterior chamber of the eye is an immune-privileged site. This allows the acceptance of allografts with lower risks of transplantation rejections. The viability of using tissue-engineered hCENC constructs together with Descement stripping and automated endothelial keratoplasty (DSAEK) technique in rabbit model has been described in the art, whereby cultured hCENC were seeded on sheets of collagen and transplanted into rabbits. These sheets showed similar cell morphology as hCENC. Since then, hCENCs have been successfully transplanted into animal models and demonstrated its therapeutic efficiency for clinical therapy. Recently, the derivation of corneal endothelial-like cells from rat neural crest cells had been described. This opens the possibility of deriving hCENC from other cell sources such as hPSCs. One of the unique features of hPSCs is its ability to self-renew and expand indefinitely. Hence, hPSCs are a very attractive surrogate cell source for generating hCENC. However, directed differentiation of hPSCs is often not an efficient process, hence the ability to enrich for the cells of interest will be necessary. Furthermore, the lack of characterization tools has so far deterred the use of cultured hCENC for transplantation.

In another point, cultured hCENCs are characterized, i.e. visually, predominantly by their 'cobblestone-like' morphological appearance. Immunostaining with zonula occludins-1 (ZO-1) and sodium potassium ATPase ($Na^+K^+$ ATPase) have also been used frequently as markers for characterization of these cells. However, these markers are not hCENC-specific and are found ubiquitously expressed in many other cell types. Therefore, both ZO-1 and $Na^+K^+$ ATPase are not ideal markers for cell isolation and enrichment. Hence, there is a need for improved methods for specifically identifying and isolating hCENCs.

SUMMARY OF THE INVENTION

In the first aspect, the present invention refers to an antibody or an antigen binding portion thereof, that binds specifically to human corneal endothelial cells (hCENCs), wherein the target of the monoclonal antibody, or antigen binding portion thereof, is essentially cell surface-expressed Peroxiredoxin-6 (Prdx6).

In a second aspect, the present invention refers to a method for determining suitability of a cell sample for corneal transplantation, wherein the method comprises: contacting a sample of donor cells obtained from a patient with an antibody as previously described; measuring an antibody binding signal; wherein an increased antibody binding signal compared to a control signal indicates a cobblestone-like cell morphology and thus suitability of the cell sample for corneal transplantation; wherein the control signal is obtained empirically from measuring multiple cell samples with known morphologies.

In a third aspect, the present invention refers to a method for quantitative enrichment of human corneal endothelial cells from a mixture of cells, wherein the method comprises the use of an antibody, or an antigen binding portion thereof, according to any one of the preceding claims.

In a fourth aspect, the present invention refer to a method of isolating viable human corneal endothelial cells from a mixture of cell, wherein the method comprises the use of an antibody, or an antigen binding portion thereof, as previously described.

In a fifth aspect, the present invention refers to a hybridoma cell line with the deposition number of PTA-121135.

In a sixth aspect, the present invention refers to a method of generating monoclonal antibodies, as described previously, by culturing hybridoma cells with the deposition number PTA-121135.

DEPOSIT OF BIOLOGICAL MATERIAL

A hybridoma cell line in accordance with the present invention has been deposited under the terms of the Budapest Treaty as follows:
  (1) Accession Number: ATCC PTA-121135
  (2) Date of Deposit: Mar. 20, 2014
  (3) Identification: Hybridoma Cell Line TAG-2A12
  (4) Depository: ATCC American Type Culture Collection, 10801 University Blvd., Manassas, Va. 20110-2209, United States of America.

BRIEF DESCRIPTION OF THE DRAWINGS

The invention will be better understood with reference to the detailed description when considered in conjunction with the non-limiting examples and the accompanying drawings, in which:

FIG. 8 shows nucleotide, peptide and CDR sequencing information for the heavy and light chains of TAG-2A12. (A) shows the heavy chain sequence, B) shows the light chain sequence and (C) the respective CDR sequences. Cells from the cadaveric corneal endothelial monolayer were use as the immunogenic agent in the generation of, among other antibodies, TAG-2A12. The hosts used for this method were SCID-mice and the isotype generated was anti-mouse IgG1.

FIG. 9 shows the sequence coverage of the antibody TAG-2A12 with the target antigen Peroxiredoxin-6 (Prdx6). The sequence match was determined to be 20%, i.e. 44/224. The underlined sections show the peptides that were identified using mass spectrometry.

FIG. 10 depicts a table of data on the comparison of TAG-2A12 with other known hCENC monoclonal antibodies. This comparison includes antigen target, molecular weight in hCENCs, molecular weight in other cell lines and sequence homology to Prdx-6 as determined using uniProt BlastP. This comparison shows a significant difference in binding sites and target antigen between known antibodies and TAG-2A12 and TAG-1A3.

DETAILED DESCRIPTION OF THE PRESENT INVENTION

Figure 1:
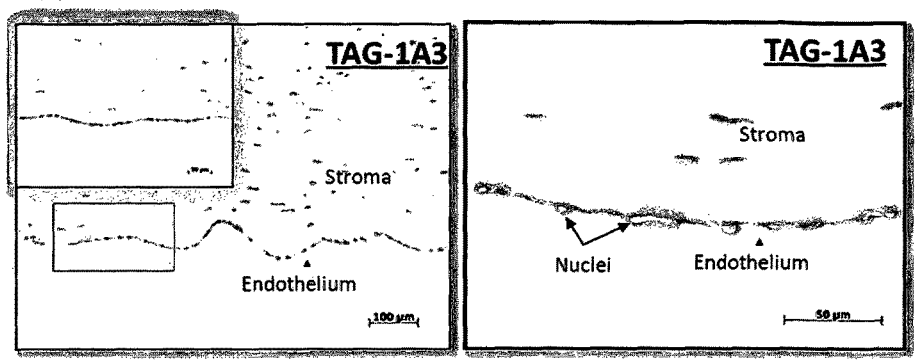
FIG. 1 shows images of immunocytochemistry of frozen cornea tissue sections in negative images. The antibodies used in sections (A) and (B) are TAG-1A3 and TAG-2A12, respectively, which bind to hCENCs. Primary antibodies were detected with Alexa Fluor 488 secondary antibody (depicted by grey staining as shown by arrow) and nuclei of cells were stained with DAPI (depicted by grey spots). Both TAG-1A3 and TAG-2A12 had shown specific of staining for the endothelium layer in corneal tissue section.
Figure 1:
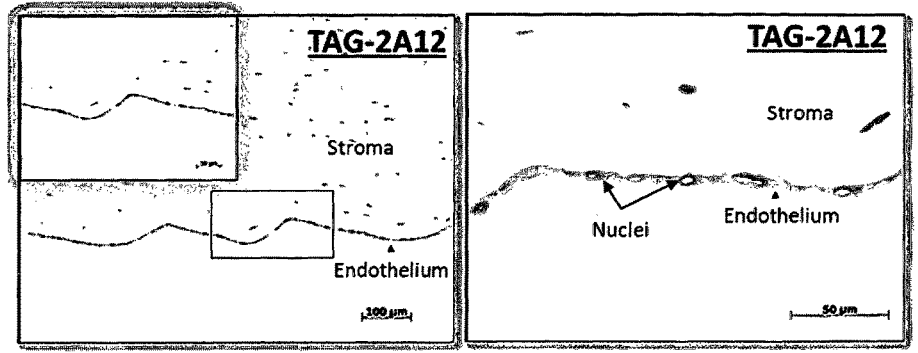

The present invention refers to the discovery and use of novel, monoclonal antibodies for the enrichment and characterization of human corneal endothelial cells. The human corneal endothelium is the most important monolayer of cells in the cornea. Human corneal endothelial cells (hCENCs), however, have very limited proliferative capacity in vivo and the density of hCENCs in the cornea is known in the art to decreases with age. Currently, cornea transplantation is used to treat irreversible damage to the corneal endothelium layer. The availability of cornea for transplantation is limited due to the scarcity of fresh corneas from suitable donors. To overcome this limitation, isolation and expansion of hCENCs have been regarded as a potential source of cells for replacing damaged corneal endothelium. As previously mentioned, the availability of fresh corneas for isolation is also limited and the ability if cell expansion is restricted as well. Other potential sources of hCENCs include differentiated populations from human pluripotent stem cells (hPSC), which may help to circumvent the limited availability of hCENCs for transplantation. However, this can only be achieved if an appropriate marker for enrichment of hCENCs from differentiated hPSC is available. In light of this issue, an antibody, such as a monoclonal or polyclonal antibody, or an antigen binding portion thereof that binds specifically to a human corneal endothelial cell (hCENC), wherein the target of the monoclonal antibody, or antigen binding portion thereof, is cell surface-expressed Peroxiredoxin-6 (Prdx6), is described herein. The term "human corneal endothelial cells" (hCENCs), as used herein, refers to cells that are isolated from a human cornea. These hexagonal cells represent one of the five distinct layers of the human cornea, and are attached to the rest of the cornea via the Descemet's layer. Having an hCENC-specific marker is one of the key tools for characterization and enrichment of cultured hCENCs. Currently, cultured hCENCs are characterized predominantly by their "cobblestone-like" morphological appearance. Immunostaining with zonula occludins-1 (ZO-1) and sodium potassium ATPase ($Na^+K^+$ ATPase) is also frequently used as markers for characterization of these cells. However, these are not hCENC-specific markers as they are ubiquitously expressed in many other cell types and are thus not suitable for cell isolation and enrichment.

Exemplary antibodies shown here, e.g. the monoclonal antibody (mAb) TAG-2A12, were chosen from a panel of monoclonal antibodies generated using cadaveric hCENCs, the method of which is disclosed in the experimental section of this application. In one example, the antibody is an antibody or antigen binding portion thereof, wherein the complementarity determining regions are selected from a group consisting of heavy chain CDR 1 (GYAFTSYNMY; SEQ ID No. 1), heavy chain CDR 2 (YIDPYNGGTSYN-QKFKG; SEQ ID No. 2), heavy chain CDR 3 (PI-YDGYYGWYFDV: SEQ ID No. 3), light chain CDR 1 (SASSSVSYMY; SEQ ID No. 4), light chain CDR 2 (LTSN-LAS; SEQ ID No. 5) and light chain CDR 3 (QQWSSNPLT; SEQ ID No. 6). These immunization-generated antibodies were screened with flow cytometry using cultured hCENCs, whereafter the positive clones were subjected to immunostaining with frozen human cornea tissue. As a result, only mAbs that specifically stained the corneal endothelial monolayer were selected (Table 1). These selected mAbs were then subjected to a secondary screening step using lung fibroblast cells, human embryonic cells and hESC-derived neural crest cells. Based on this further specificity, the antibody TAG-2A12 was selected for further analysis.

In another example, the antibody or an antigen binding portion as described herein may include, but is not limited to, Fab, Fab', F(ab')2, Fv, diabodies, Fd, dAb, maxibodies, single chain antibody molecules, complementarity determining region (CDR) fragments, scFv, diabodies, triabodies, tetrabodies and polypeptides that contain at least a portion of an immunoglobulin, wherein the portion of an immunoglobulin is sufficient to confer specific antigen binding to a target polypeptide.

As used herein, the term "antibody" includes reference to both glycosylated and non-glycosylated immunoglobulins of any isotype or subclass, or to an antigen-binding region thereof, or fragment thereof, that competes with the intact antibody for specific binding, unless otherwise specified, including human, humanized, chimeric, multi-specific, bispecific, monoclonal, polyclonal, and oligomers or antigen-binding fragments thereof. Also included are proteins having an antigen binding fragment or region such as Fab, Fab', F(ab')2, Fv, diabodies, Fd, dAb, maxibodies, single chain antibody molecules, complementarity determing region (CDR) fragments, scFv, diabodies, triabodies, tetrabodies and polypeptides that contain at least a portion of an immunoglobulin that is sufficient to confer specific antigen binding to a target polypeptide. The term "antibody" is inclusive of, but not limited to, those that are prepared, expressed, created or isolated by recombinant means, such as antibodies isolated from a host cell transfected to express the antibody. In additional examples, antigen-binding fragments are produced by enzymatic or chemical cleavage of intact antibodies. Antibody-binding fragments include, but are not limited to, Fab, Fab', F(ab')2, Fv, and single-chain antibodies. In certain examples, binding fragments are produced by recombinant DNA techniques.

The term "heavy chain", in reference to an antibody, includes a full-length heavy chain, and fragments thereof, having sufficient variable region sequence to confer specificity for a specified antigen or target. A full-length heavy chain includes a variable region domain, $V_H$, and three constant region domains, $C_H1$, $C_H2$, and $C_H3$. The $V_H$ domain is at the amino-terminus of the polypeptide, and the $C_H3$ domain is at the carboxyl-terminus. Heavy chains are classified as mu, delta, gamma, alpha, or epsilon, and define the antibody's isotype as IgM, IgD, IgA, and IgE, respectively.

The term "light chain", in reference to an antibody, includes a full-length light chain, and fragments thereof, having sufficient variable region sequence to confer specificity for a specified antigen or target. A full-length light chain includes a variable region domain, $V_L$, and a constant region domain, $C_L$. Like the heavy chain, the variable region domain of the light chain is at the amino-terminus of the polypeptide. Human light chains are classified as kappa and lambda light chains.

"CDRs" are defined as the complementarity determining region amino acid sequences of an antigen binding protein. These are the hypervariable regions of immunoglobulin heavy and light chains. There are three heavy chain and three light chain CDRs (or CDR regions) in the variable portion of an immunoglobulin. Thus, "CDRs" as used herein refers to all three heavy chain CDRs, all three light chain CDRs, all heavy and light chain CDRs, or at least two CDRs.

Throughout this specification, amino acid residues in variable domain sequences and full length antibody sequences are numbered according to the Kabat numbering convention. Similarly, the terms "CDR", "CDRL1", "CDRL2", "CDRL3", "CDRH1", "CDRH2", "CDRH3" used in the disclosure follow the Kabat numbering convention. It will be apparent to those skilled in the art that there are alternative numbering conventions for amino acid residues in variable domain sequences and full length antibody sequences. There are also alternative numbering conventions for CDR sequences, for example those set out in Chothia et al. (1989) Nature 342: 877-883. The structure and protein folding of the antibody may mean that other residues are considered part of the CDR sequence and would be understood to be so by a skilled person.

The "framework regions" of antibodies are defined as amino acid sequences interposed between CDRs, including variable light and variable heavy framework regions. The framework regions serve to hold the CDRs in an appropriate orientation for antigen binding.

As described herein, the antibody, or antigen binding portion thereof, may be of polyclonal or monoclonal origin. In another example, the antibodies as disclosed herein are generated by culturing hybridoma cells with the deposition number PTA-121135. In a further example, the hybridoma cell line has the deposition number of PTA-121135.

Antibodies or fragments thereof, in accordance with the invention, are prepared utilizing antibody production methods known in the art. The antibodies may be produced using methods selected from a group consisting of the hybridoma method, recombinant methods, chimeric methods, antibody isolation and antibody purification methods. Exemplary use of the hybridoma method can be found in the experimental section of the present disclosure.

As referenced herein, the methods used for the isolation and purification of antibodies may include, but are not limited to ultrafiltration, dialysis, centrifugation, ion exchange chromatography, size exclusion chromatography, affinity chromatography, precipitation, gel filtration, gel electrophoresis and capillary electrophoresis.

Figure 4:
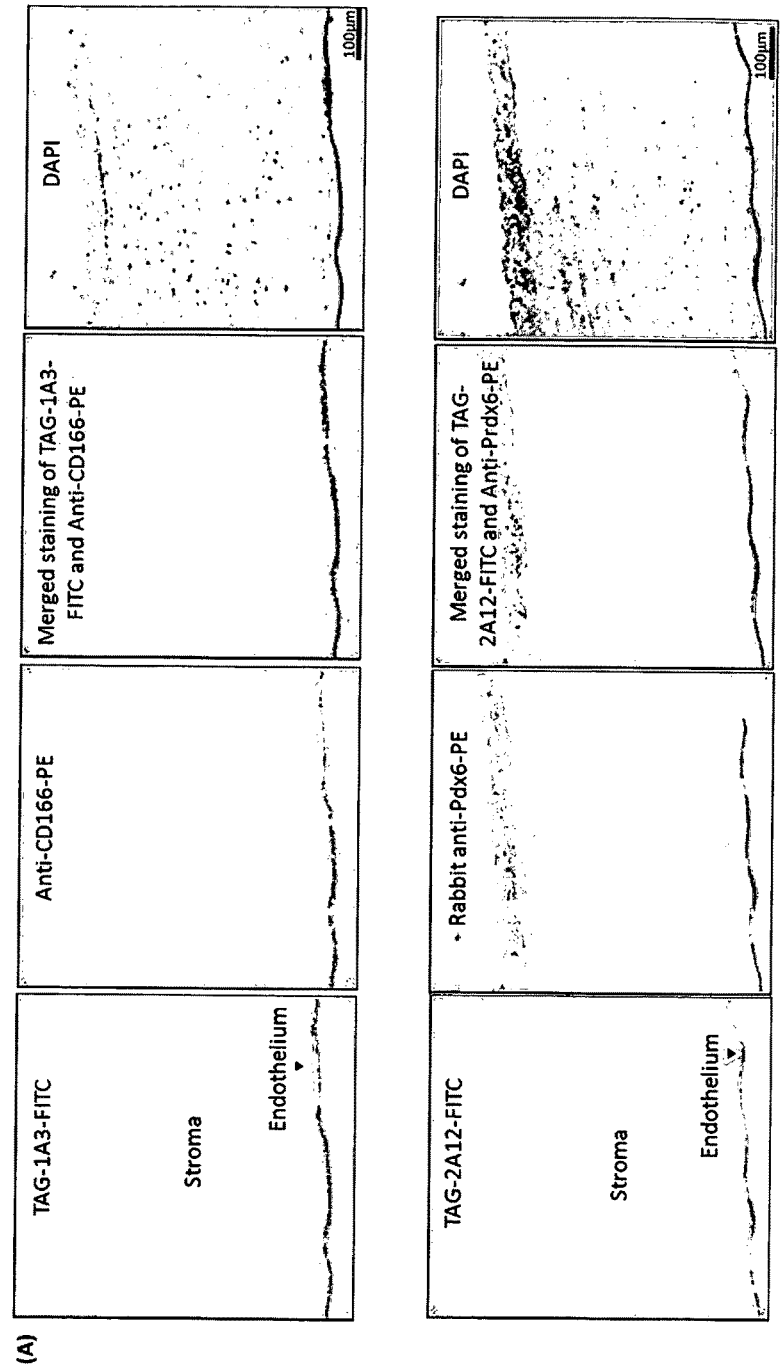
FIG. 4 shows micrograph images for comparing the staining of known antibodies vs. TAG-1A3 and TAG-2A12 on both corneal tissue sections and cultured hCENCs (in negative images). Primary antibodies were detected with Alexa Fluor (AF) 488 or AF 594 secondary antibody and nuclei of cells were stained with DAPI; these images show the staining of frozen corneal tissue. Both known antibodies and in-house antibodies showed specific staining of the endothelium layer. Section (B) shows the staining of cultured hCENCs. Cells were stained with an isotype antibody as negative control, and ZO-1 staining was used a positive control. Staining pattern for TAG-1A3 appeared more membrane-like similar to known anti-CD166. Membrane localization of TAG-2A12 was shown as compared to known anti-Prdx6 antibody where more intracellular staining was observed.
Figure 4:
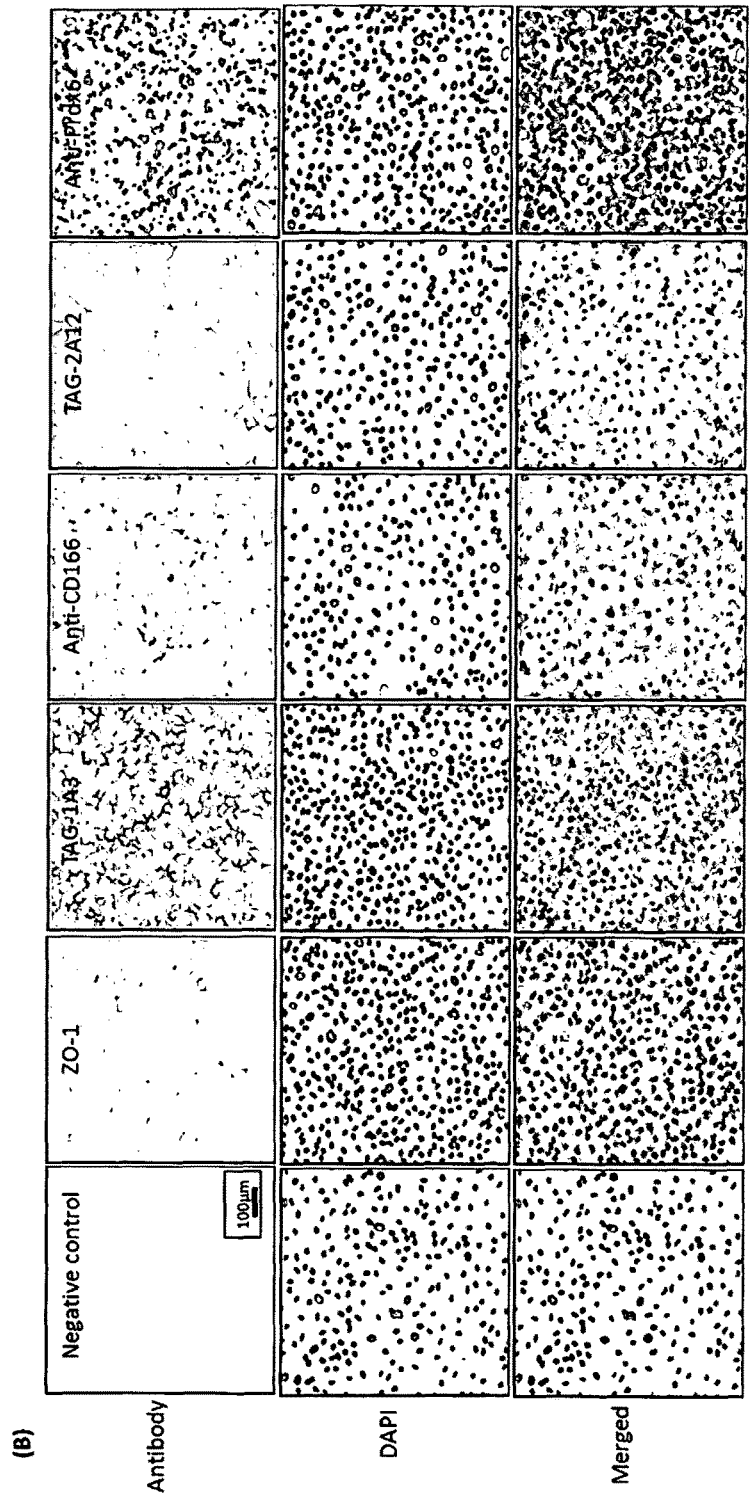

Described herein are monoclonal or polyclonal antibodies that bind specifically to hCENCs, more exactly monoclonal antibodies, wherein the target of the monoclonal antibody, or antigen binding portion thereof, is cell surface-expressed Peroxiredoxin-6 (Prdx6). The identity of this target antigen was determined using immunoprecipitation, as well as mass spectrometry-based approach and analysis. The antigen target of TAG-2A12 was also determined using reverse immunoprecipitation and utilizing a known antibody as a control, as shown in the experimental section of this application. As shown in the results, while both antibodies (TAG-2A12 and the known anti-Prdx6, FIG. 4) stained positive on the corneal endothelial monolayer on the corneal tissue, only mAb TAG-2A12 stained membrane bound Prdx6, whilst the known anti-Prdx6 only stained for intracellular Prdx6. Furthermore, when analysed using flow-cytometry it was observed that only TAG-2A12 was able to detect Prdx6 antigen target expressed on the surface of hCENCs.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The protein Prdx6 is a bifunctional enzyme with two distinct active sites and is encoded by the gene of the same name. It is a member of the thiol-specific antioxidant protein family and is involved in redox regulation of the cell, via its capability to reduce $H_2O_2$, short chain organic fatty acids, and phospholipid hydroperoxides. It plays a possible role in the regulation of phospholipid turnover, as well as in protection against oxidative injury.

In another example, the antibodies or an antigen binding portions thereof, do not bind significantly to cells selected from the group consisting of epithelial cells, stromal fibroblast cells, human lung fibroblasts, hESC-derived neural crest cells and human embryonic stem cells.

In a further example, the antibodies disclosed herein, or antigen binding portion thereof, do not bind to immortalized human corneal endothelial cells The term "significantly", as used herein, implies that the characteristic describes using this term has a low probability of occurring by chance. Significance may be defined, e.g. in biology as an analytical evaluation of the results of a comparative trial or survey, wherein the data yields a difference in outcome depending on treatment or environmental factors. These are considered statistically significant, if various mathematical procedures indicate there is less than five percent (5%) chance that the same results would occur through random accident. In mathematical, statistical terms this is expressed as p<0.05 i.e. the p-value is less than 0.05. If no mathematical basis for usage the term significant is given, e.g. when the population or data size is too small to enable a statistical analysis without incurring a high standard deviation, the term "significant" or "significantly" may also be understood to mean that the characteristic in question is important or meaningful for the analysis of the data as a whole.

The term "immortalized cells" or "immortalized cell lines", as used herein, refer to a cell, or a population of cells, a multicellular organism, which would normally not proliferate indefinitely but, due to mutation, has evaded normal cellular senescence and instead continues to undergo cell division. These cells can therefore be grown for prolonged periods in vitro. The mutations required for immortality can occur naturally, or be intentionally induced for experimental purposes. Immortalized cell lines may be generated using known methods, for example, hybridoma technology, or by isolating of a naturally occurring cancer cells, as these are known to be intrinsically immortal.

Figure 6:
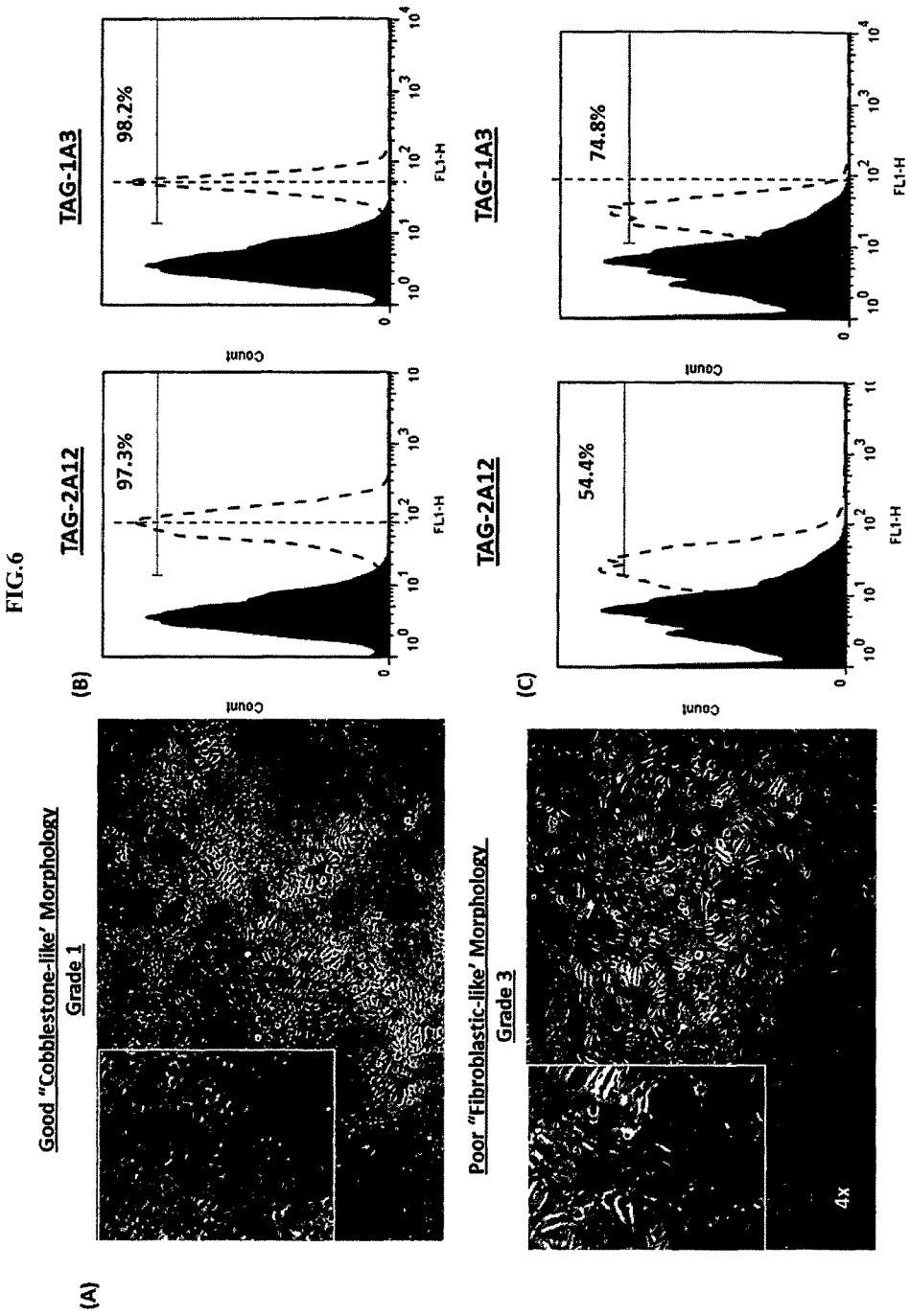
FIG. 6 shows the results of the characterization of cultured hCENCs with TAG-1A3 and TAG-2A12. Section (A) shows micrograph images of treated cells. Top panel: Cells with 'cobblestone-like' morphology and bottom panel: cells with 'fibroblastic-like' morphology. Specifically, (A) shows that cells with 'cobblestone-like' morphology have high expression of TAG-2A12, and cells of the bottom panel, displaying 'fibroblastic-like' morphology had much lower expression levels of TAG-2A12. Sections (B to C) show histograms depicting the expression of TAG-1A3 and TAG-2A12 on the cell surface via flow cytometry analysis. Specifically, section (B) shows cells with 'cobblestone-like' morphology have a higher expression of TAG-1A3 and TAG-2A12 than cells in section (C) with 'fibroblastic-like' morphology. Expression level of (A) is compared based on the mean fluorescence intensity (MFI) if the shift in the histogram (Sections B and C). Section (D) shows expression levels in nMFI (normalized mean fluorescent intensity) of TAG-1A3 and TAG-2A12 in various donor samples.
Figure 6:
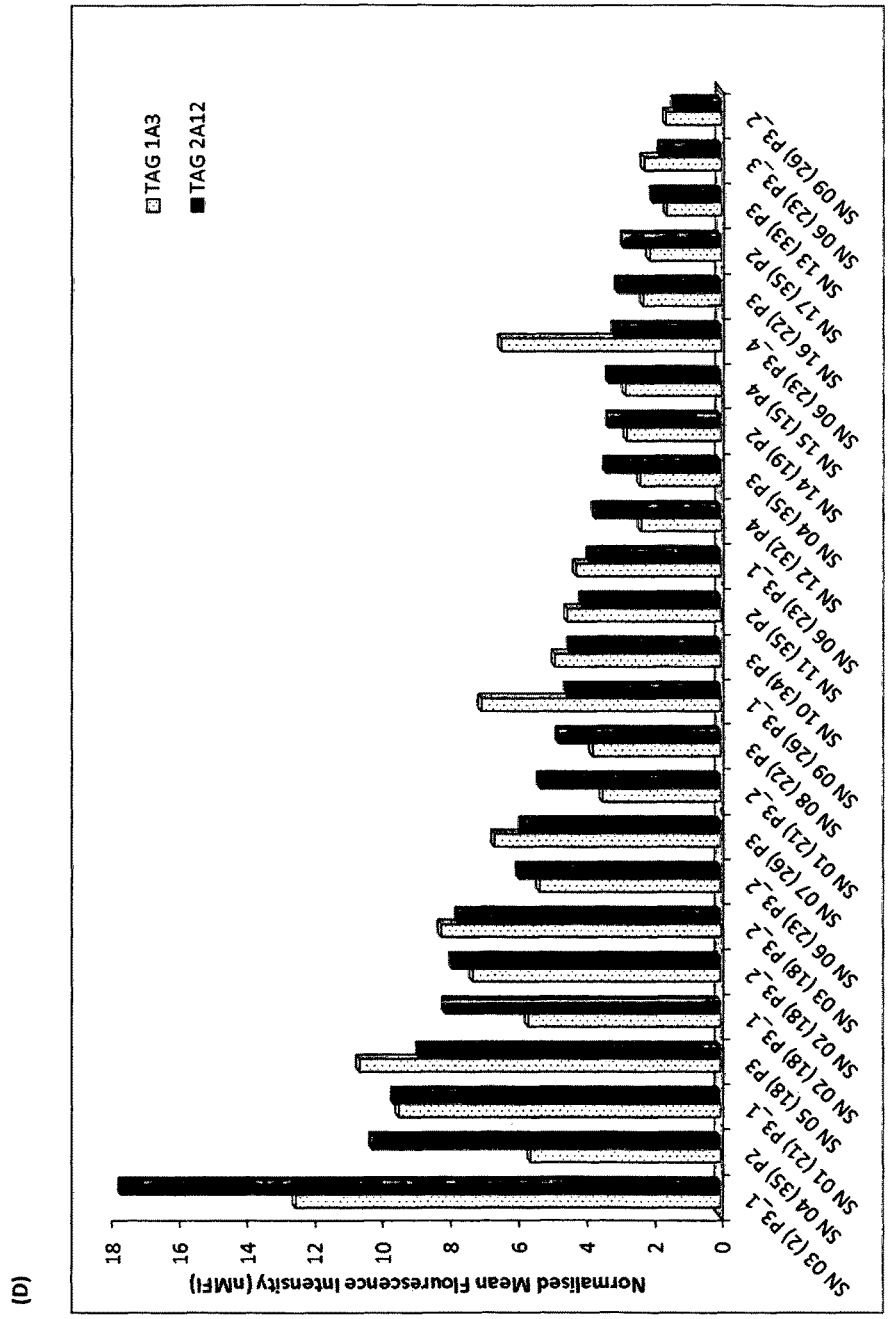

The description further provides monoclonal or polyclonal antibodies, or an antigen binding portion thereof, wherein the antibodies binds to human corneal endothelial cells in a manner in which the strength of a signal derived from the binding of the antibody to the antigen is proportional to the amount of cells exhibiting a "cobblestone-like" morphology, thus enabling a grading of the human corneal endothelial cell quality. The mAb TAG-2A12 was further used to characterize cultured hCENCs from multiple donors, the results of which are shown in FIG. 6. These results show the antibody's ability to identify all derivation of cultured hCENCs from different donors, thus validating the antibody's specificity to hCENCs. In addition, it was determined that the normalized mean fluorescent intensity (nMFI) of TAG-2A12 correlated well with the morphological grading of good "cobblestone-like" cultured hCENCs versus bad "fibroblastic-like" culture hCENCs, i.e. a better morphology correlated to a higher Prdx6 expression. These results hence demonstrate a unique expression pattern of surface Prdx6 and further show that TAG-2A12 is not only specific for hCENCs, but also provides a quantitative assessment on the state of cultured hCENCs. Results also show that the binding of TAG-2A12 to Prdx6 results in a sequence coverage of 20%, as identified by mass spectrometry.

As used herein, the term "quantitative" is understood to mean a measurement based on a quantity or number, as opposed to a measurement based on a characteristic of quality. Statements made in regards to quantity are predominantly made on an absolute numeric scale and/or in a relative, size-dependent manner, e.g. usage of the terms "more than" and "less than", in reference to known amount.

As used herein, the term "qualitative" is understood as the use of descriptions or distinctions based on a chosen quality, rather than on some quantity. In the present disclosure, the term "qualitative" refers to the morphological, visual grading of hCENCs, encompassing usage of the "cobblestone-like" morphology, denoting that hCENCs showing a cobblestone-like morphology are more suitable for corneal transplants as compared to hCENCs showing "fibroblast-like" morphology, which are defined as being less to unsuitable for corneal transplantation. Examples of a cobblestone-like and a fibroblast-like morphology can be seen in panel A of FIG. 6. As can be seen from the figure, a cobblestone-like morphology means a cell that appears to be more rounded, almost globular appearance, with less to no elongated forms, whereas a fibroblast-like morphology implies that the cell appears small, elongated to spindle-like, and tend to align locally in parallel clusters.

Also described herein is a method of isolating viable human corneal endothelial cells from a mixture of cell, wherein the method comprises the use of an antibody, or an antigen binding portion thereof. In one example, the method comprises the steps of exposing a mixture of cells to a monoclonal antibody and, in a further step, separating cells that bind to said monoclonal antibody from cells that do not bind to said monoclonal antibody.

In one example, the isolated hCENCs are viable cells. In another example, the isolated hCENCs are suitable for medical transplant and grafting purposes. In a further example, the mixture of cells, as previously mentioned, wherein the cell types utilised in the mixture are those cell types found in cell samples in a clinical setting.

As used herein, the term "cell mixture" or "mixture of cells" implies a heterogeneous collection of cells that may be found in vivo or in vitro. These cells may have been isolated from autologous, heterologous, allogeneic, syngeneic and/or xenogeneic cell sources. In the present disclosure, a cell mixture may contain cells including, but not limited to, human embryonic stem cells (hESCs), epithelial cells, stromal fibroblast cells (SF cells), progenitor cells of the ectoderm, endoderm or mesoderm, human lung fibroblasts and hESC-derived neural crest cells.

The term "exposing" refers to introducing or bringing one substance in contact with the surface or environment of another substance or object. In one example, the term pertains to the introduction of an antibody into the environment, e.g. the cell culture dish, of a cell, thus enabling the antibody to bind to the cell surface, and if capable, penetrate into the cell.

The term "viable" refers to a characteristic of cells, in vivo as well as in vitro, to be able to live and develop. For example, the usage of this term in context with an isolated cell implies that said cell, once isolated from its source, is capable of sustaining its life, and well as its proliferative capability, away from said source. As a result, when this cell is transplanted back into its original source, or into another being of the same species, it would be capable of proliferating and surviving in its new environment. This concept may be understood in a biological, as well as medical context, wherein the medical usage of the term "viable" implies the suitability and capability of a cell, or a cell mixture, for medical transplant and grafting purposes. For example, as defined in claim 1, the antibody can be defined to specifically bind to a viable cell.

As a proof of concept study, the specificity of the antibodies presented in this application was furthermore investigated in regards to their capability of enriching hCENCs within a cell culture. Hence, cell mixtures of either stromal fibroblast (SF) cells or hESCs were mixed with hCENCs and subjected to magnetic activated cell sorting (MACS), using TAG-2A12 as a cell sorting target. The negative population of SF cells or hESCs was pre-labelled with a membrane dye prior to mixing. This mixture was chosen to simulate a pseudo-real situation, in order to prove the antibody's applicability in an in vitro setting and in order to prove that the antibody is capable of differentiating between an allogenic, albeit artificial, and heterogeneous source of cells (e.g. hESCs present in donor samples) and hCENCs. Following sorting, both flow-through and eluted fractions were assessed by flow cytometry in order to determine relative populations for each of the fractions. It was shown that TAG-2A12 was capable of isolating hCENCs to a yield of 90% purity from a starting mixture with a ratio of 50:50. On the whole, it is shown that the mAb TAG-2A12 is capable of identifying hCENCs from both autologous, as well as heterologous cell sources and it also able to provide quantitative assessment (vs. morphological assessment) of the hCENCs detected. In other examples, the present invention includes methods of separation selected from a group consisting of column chromatography, magnetic affinity cell separation and fluorescence-activated cell sorting.

The methods utilised for cell sorting, more generally known as "sorting" or "separation methods", are known in the art and may be selected from a group consisting of magnetic affinity cell separation (MACS), fluorescence activated cell sorting (FACS), flow cytometry, single cell sorting methods, lab-on-chip arrays, microrafts, and centrifugation.

Described herein is a method for determining suitability of a cell sample for corneal transplantation, wherein the method comprises contacting a sample of donor cells obtained from a patient with an antibody as previously described; measuring an antibody binding signal, wherein an increased antibody binding signal compared to a control signal indicates a cobblestone-like cell morphology and thus suitability of the cell sample for corneal transplantation; wherein the control signal is obtained empirically from measuring multiple cell samples with known morphologies.

This method pertains to the usage of the herein disclosed antibodies in determining how suitable a cell sample is for corneal transplantation, wherein the comparison of antibody binding signal of the donor sample is compared to antibody binding of the same antibody to a control cell sample, thus giving a semi-quantitative, relative assessment of the quality of the donor sample. This implies the use of the same antibody for both samples, as well as knowledge of the morphology, as well as the viability, of the control cells. This comparison may be made in a directly correlative manner, i.e. if the antibody binding signals of both the control sample and that of the donor sample are similar, and it is known that the control samples exhibit the qualities required of a cell suitable for transplant, then the donor sample is suitable for transplant; or in a inversely correlative manner, i.e. if the antibody binding signal of the control sample is lower than that of the donor sample, but the control sample is known to display undesired characteristic or an undesired morphology, then the donor sample is unsuitable for transplant. The comparison of the donor antigen binding signal may also be made to a control antigen binding signal, which had been obtained empirically through the measurement of cell samples with known morphologies, using the same antibodies. As defined previously, in one example, a cobblestone-like morphology, understood as being a desirable characteristic, has a high antigen binding signal, whereas a fibroblast-like morphology, understood as being an undesirable characteristic, has a low antigen binding signal.

Further described herein is a tool for quantitative enrichment, as well as qualitative isolation, of hCENCs. Such cells can be used for treating corneal diseases, which can be treated by corneal transplantations.

Known corneal diseases include, but is not limited to bullous keratopathy, Keratitis resulting from perforation—affecting corneal endothelium, Fuchs' endothelial dystrophy, mechanical trauma, physical damage to the corneal endothelium, Posterior Polymorphous Dystrophy, Congenital Hereditary Endothelial Dystrophy, Iridocorneal endothelial syndrome (ICE syndrome), Toxic anterior segment syndrome (TASS), infectious endothelitis (e.g viral endothelitis (HSK/CMV), bacterial endothelitis, parasitic endothelitis and X-linked endothelial corneal dystrophy.

Other indications for corneal transplantation include optical, tectonic, reconstructive, therapeutic and cosmetic. Examples for optical indications include replacing the opaque or distorted host tissue with clear healthy donor tissue in order to improve visual acuity. The most common indication in this category is pseudophakic bullous keratopathy, keratoconus, corneal degeneration, keratoglobus and dystrophy, as well as scarring due to keratitis and trauma. Examples for tectonic/reconstructive corneal transplantations are preservation of corneal anatomy and integrity in patients with stromal thinning and descemetoceles and reconstruction of the anatomy of the eye, e.g. after corneal perforation. Examples for therapeutic corneal transplantation include removal of inflamed corneal tissue unresponsive to treatment by antibiotics or antivirals; and an example of the use cosmetic corneal transplantation being the improvement in appearance of patients with corneal scars that have given a whitish or opaque hue to the cornea.

EXAMPLES

Example 1

Generation of hCENC Specific Monoclonal Antibodies (mAbs)

As known in the art, the isolation of human corneal endothelial cells occurs via a two-step process of peeling off the Descemet's membrane-endothelial layer off the donor cornea and then exposing the isolated cells to enzymatic digestion using collagenase, dispase or trypsin/EDTA. A drawback of this method is that stromal keratocytes may be present in the sample which, due to the slow proliferative nature of the hCENCs, will become fibroblastic and overtake the culture. hCENCs in culture tend to become more heterogeneous over time, as a more fibroblastic morphology can found among cultured cells with high passage numbers. Furthermore, it is known in the art that hCENC cultures established from older donors proliferate slower and to a lesser extent, as well as displaying a higher heterogeneity compared to hCENC cultures established from younger donors.

The availability of validated hCENC markers allows investigators to better characterize these cells cultured in various media and derived from different platforms. The use of a panel of monoclonal antibodies (mAbs) specific to hCENC will enable researchers to establish reference guidelines during ex-vivo expansion prior to any transplantation studies. In the present example, a panel of mAbs is shown, the focus being on TAG-1A3 and TAG-2A12, which, by recognizing cell surface antigens expressed on hCENC, are able to quantitatively distinguish between populations of hCENC with desirable morphology and populations of hCENC with undesired characteristics. As a result, characterization of cultured hCENC can be improved during their expansion phase and prior to transplantation.

Using cadaveric hCENC, a total of 389 hybridoma clones were generated from the immunization. Supernatants from these clones were used to screen cultured hCENC for positive binding using flow cytometry. Only 18 mAbs were found to be binding to at least 20% of the cell population of hCENC, as shown in Table 1 below:

TABLE 1

Binding analysis of monoclonal antibodies (mAbs) to various cell lines. As a selection criterion, mAbs derived from the immunization panel were subjected to binding analysis with the primary immunogenic cell line (hCENCs), as well as other cell lines. The analysis was done using flow cytometry. Cells with greater than 80% of binding (M-gating) with respect to the isotype control were denoted by '+++'; cells with binding of 60%-80% were denoted by '++'; cell with binding of 40%-60% were denoted by '+'; cell with binding of 20%-40% were denoted by '+/−'; and cells with binding <20% were denoted by '−'.

| mAb | hCENC | HES-3 | H9 | Neural Crest | IMR90 |
| --- | --- | --- | --- | --- | --- |
| TAG-1A3 | +++ | +/− | +/− | +++ | +++ |
| TAG-1C5 | +++ | + | +++ | +++ | +++ |
| TAG-1D5 | ++ | +++ | +++ | +/− | + |
| TAG-1E6 | +++ | +++ | +++ | +++ | +++ |
| TAG-1G2 | +++ | − | − | +++ | + |
| TAG-1G4 | +++ | +++ | ++ | +++ | +++ |
| TAG-1G5 | ++ | +++ | +++ | + | + |
| TAG-1H1 | +/− | +/− | − | +/− | +++ |
| TAG-1H2 | ++ | +++ | ++ | + | + |
| TAG-1H7 | +++ | − | +++ | +++ | +++ |
| TAG-2A12 | +++ | − | − | − | − |
| TAG-2B8 | +++ | +++ | +++ | +++ | +++ |
| TAG-2G3 | ++ | +++ | ++ | +/− | +/− |
| TAG-2G7 | +/− | ++ | +++ | − | − |
| TAG-2G10 | +++ | +++ | +++ | +++ | +++ |
| TAG-3B11 | +++ | − | − | − | + |
| TAG-3C4 | +++ | +++ | ++ | − | +/− |

TABLE 1-continued

Binding analysis of monoclonal antibodies (mAbs) to various cell lines. As a selection criterion, mAbs derived from the immunization panel were subjected to binding analysis with the primary immunogenic cell line (hCENCs), as well as other cell lines. The analysis was done using flow cytometry. Cells with greater than 80% of binding (M-gating) with respect to the isotype control were denoted by '+++'; cells with binding of 60%-80% were denoted by '++'; cell with binding of 40%-60% were denoted by '+'; cell with binding of 20%-40% were denoted by '+/−'; and cells with binding <20% were denoted by '−'.

| mAb | hCENC | HES-3 | H9 | Neural Crest | IMR90 |
|---|---|---|---|---|---|
| TAG-3G2 | +++ | − | − | − | − |
| Legend | +++ | ++ | + | +/− | − |
| % binding (M-Gate) | >80% | 60-80% | 40-60% | 20-40% | <20% |

Binding specificity of these mAbs was further determined by tissue staining with frozen human cornea sections. The data indicated that only two out of the 18 mAbs, TAG-1A3 and TAG-2A12, bound specifically to the corneal endothelial monolayer of the tissue section (FIG. 1 and Table 2) and no staining was observed on the epithelial or stromal layers.

TABLE 2

Tissue section immunocytochemistry (ICC) of various mAbs on frozen corneal tissue Primary antibodies were detected with Alexa Flour (AF) 488 or AF 594 secondary antibody and nuclei of cells wen stained with DAPI. Only TAG-1A3 and TAG-2A12 showed specificity of staining for the endothelium layer in corneal tissue section.

| | Tissue sections | | |
|---|---|---|---|
| mAbs | Endothelium | Stroma | Epithelium |
| TAG-1A3 | +++ | − | − |
| TAG-1C5 | − | − | − |
| TAG-1D5 | +++ | − | +++ |
| TAG-1E6 | +++ | +++ | +++ |
| TAG-1G2 | − | − | + |
| TAG-1G4 | − | − | + |
| TAG-1G5 | +++ | − | ++ |
| TAG-1H1 | + | − | + |
| TAG-1H2 | +++ | − | ++ |
| TAG-1H7 | +++ | +++ | +++ |
| TAG-2A12 | +++ | − | − |
| TAG-2B8 | + | ++ | + |
| TAG-2G3 | +++ | − | + |
| TAG-2G7 | ++ | − | + |
| TAG-2G10 | + | + | + |
| TAG-3B11 | − | − | − |
| TAG-3C4 | + | + | + |
| TAG-3G2 | +++ | +++ | +++ |

Legend
+++ Strong binding
++ Mid binding
+ Weak binding
− No binding

Figure 2:
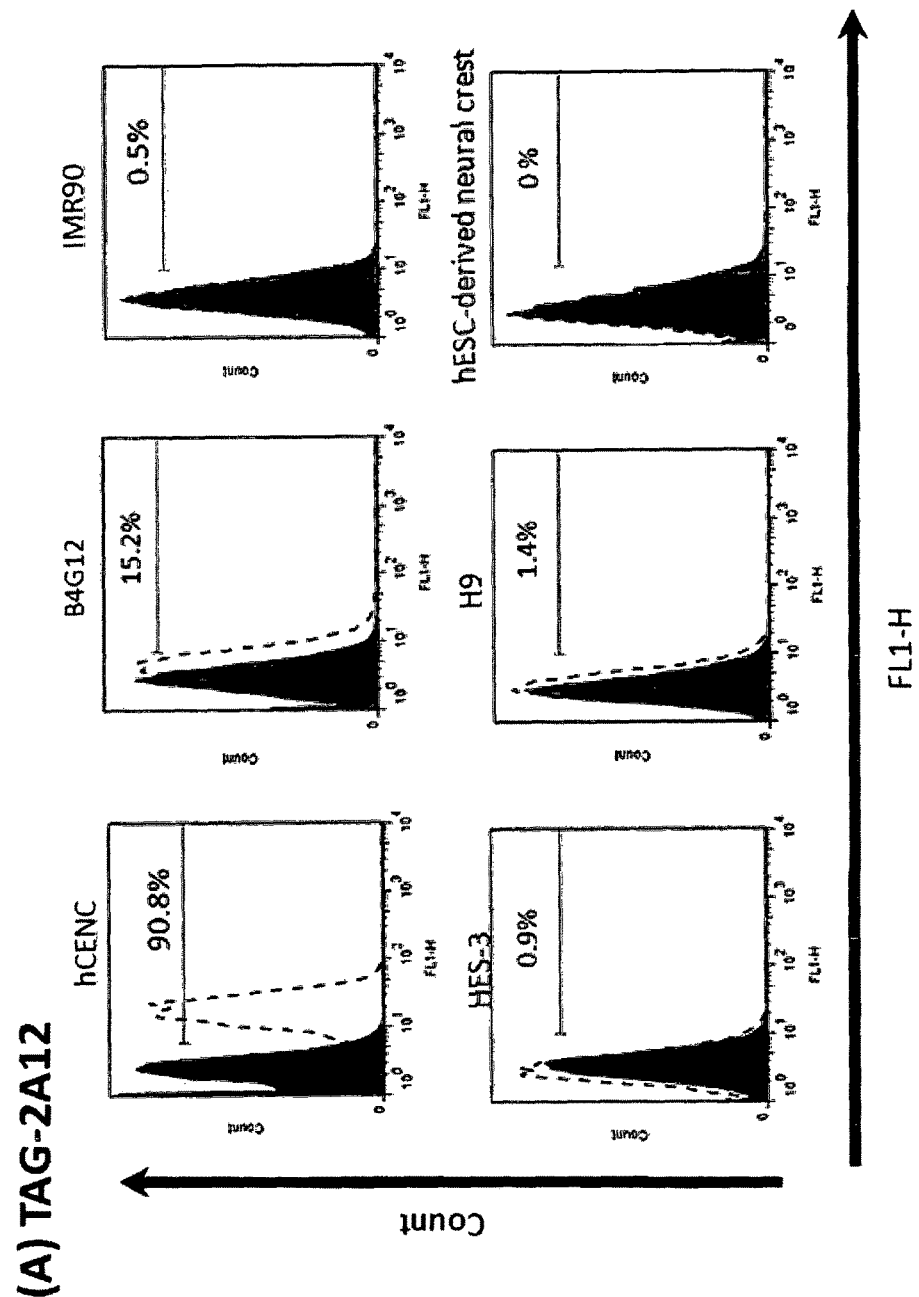
FIG. 2 shows the results of a histogram analysis of TAG-2A12 (A) and TAG-1A3 (B and C) in various cell lines, namely hCENC, B4G12, IMR90, HES-3, H9 and hESC-derived neural crest cells. The shaded area represents the isotype control and dotted line/unshaded area represents antibody staining. TAG-1A3 was binding to different cells lines with varying normalized mean fluorescence intensity (nMFI) and higher nMFI values were observed with both hCENC and hESC-derived neural crest cells. TAG-2A12 was found to be binding specifically to hCENC only, whereby the specificity was seen to be higher than 90%. Section (C) shows column graphs depicting the normalized mean fluorescence intensity (nMFI) of TAG-1A3 on various cell lines. nMFI is calculated using MFI of sample/MFI of isotype control. TAG-1A3 had high nMFI levels compared to the other cell lines.
Figure 2:
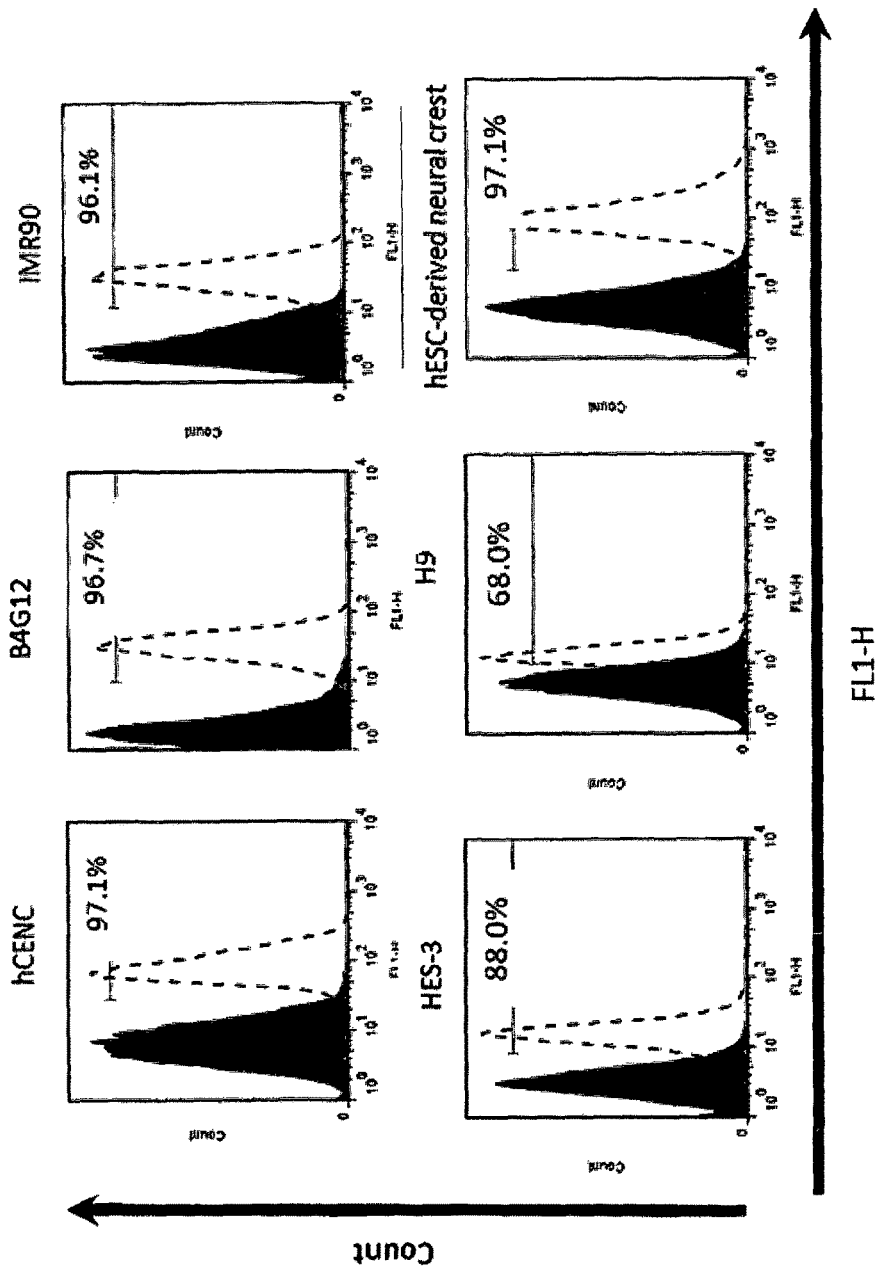
Figure 2:
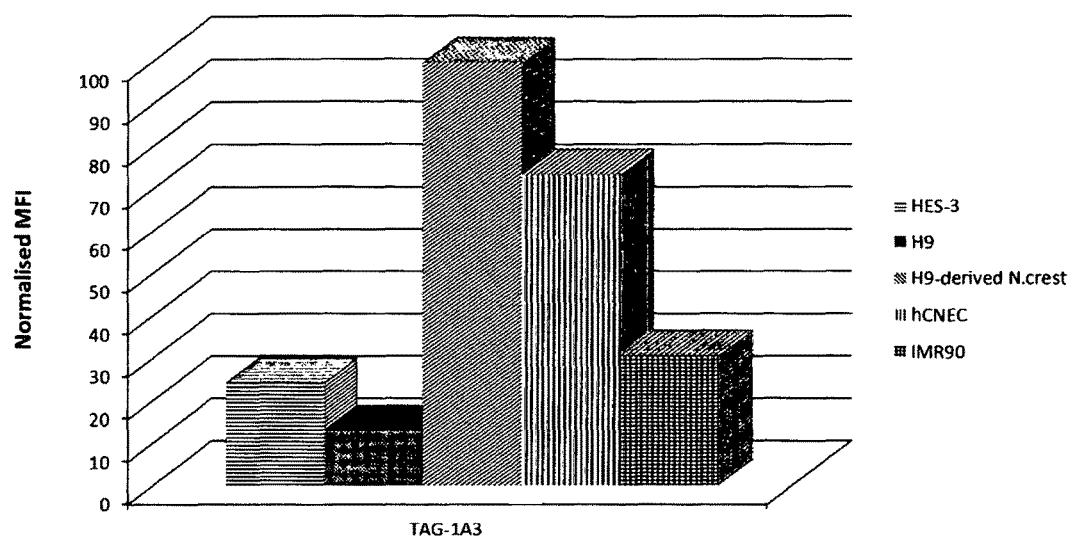

Next, the binding of TAG-1A3 and TAG-2A12 to an immortalized hCENC cell line, B4G12, was investigated. The results demonstrated that only TAG-1A3 bound to B4G12 but not TAG-2A12 (as shown in FIG. 2). To further assess the specificity of these mAbs, screening was also conducted on a panel of other cell types such as lung fibroblasts (IMR90), human embryonic stem cell lines (HES-3 and H9) and H9-derived neural crest cells. Interestingly, only TAG-2A12 demonstrated high binding specificity to hCENC, (>90% TAG-2A12 +ve) whilst no binding was observed for all the other cells types screened (FIG. 2 and Table 1). Hence, TAG-2A12 has been shown to not bind to immortalized human corneal endothelial cells. In contrast, even though TAG-1A3 bound to more than 90% of hCENC, the protein it targets is also expressed on other cell types with varying degree of TAG-1A3 binding based on its normalized mean fluorescence intensity (nMFI; FIG. 2C). However, TAG-1A3 had the highest nMFI for hCENC compared to both hESC and hESC-derived neural crest cells, suggesting a higher expression level of the antigen target on hCENC.

Example 2

Characterization of Antigen Targets

In order to identify the antigen target of TAG-1A3 and TAG-2A12 on hCENCs, a series of experiments involving estimating the molecular weight of the cell surface protein by Western blotting, immunoprecipitation (IP), silver-staining, mass spectrometry, and finally validation with known mAbs were carried out.

Figure 3:
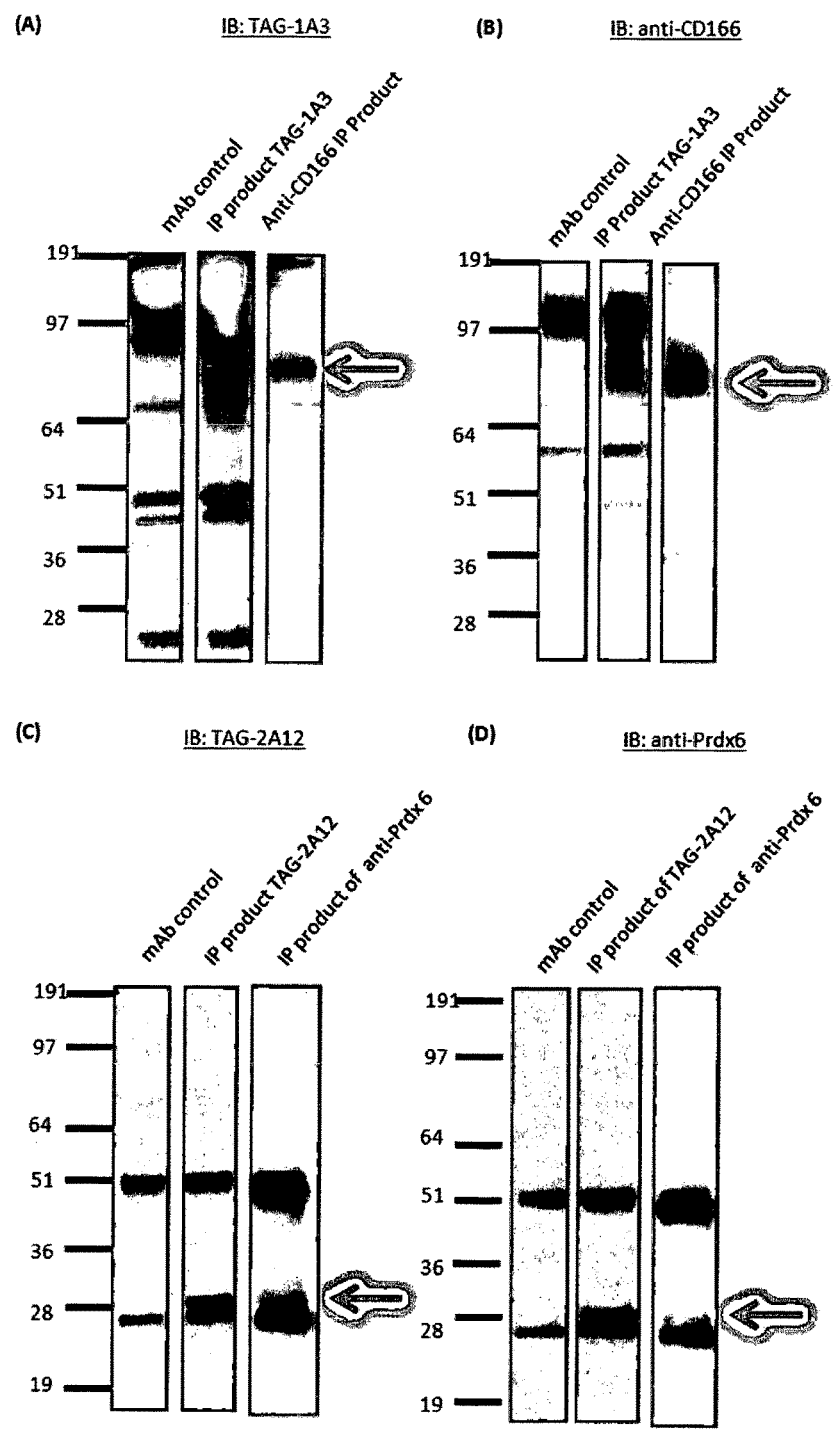
FIG. 3 shows the result of immunoprecipitation for antigen target identification of monoclonal antibodies (mAb) TAG-1A3 and TAG-2A12. The immunoprecipitation (IP) was conducted using TAG-1A3 and known CD166 and immunoblotted (IB) with (section A) TAG-1A3 and (section B) anti-CD 166 respectively. Results shows both forward and reverse-IP using the TAG-1A3 and CD166 are enriching for the same antigen bands between 64 kDa and 97 kDa suggesting that TAG-1A3 and CD166 are targeting at the same antigen. The same method was conducted using TAG-2A12 and known Peroxiredoxin-6 (Prdx6) for IP, and (section C) TAG-2A12 and (section D) Prdx6 for IP, respectively. Results shows both forward and reverse-IP using the TAG-2A12 and Prdx6 are enriching for the same antigen bands between 28 kDa and 36 kDa suggesting that the mAb may be targeting at the same antigen.

By Western blotting, TAG-1A3 and TAG-2A12 were found to bind to protein bands corresponding to approximately 90 kDa and 28 kDa respectively (FIGS. 3A and 3C, Panel 2). Immunoprecipitation using TAG-1A3 and TAG-2A12 successfully enriched for the antigen targets (FIGS. 3A and 3C Panel 2). The immunoprecipitation products of TAG-1A3 and TAG-2A12 were excised from a duplicate silver stained gel and sent for identification using LC/MS-MS. After database search using the MS data, the putative antigen target that TAG-1A3 enriched for was ALCAM/CD166, while peroxiredoxin-6 (Prdx6) was detected by TAG-2A12. To validate the antigen targets, known antibodies against ALCAM/CD166 and Prdx6 were used.

The samples from immunoprecipitation using TAG-1A3 and TAG-2A12 were immunoblotted against their respective known antibodies. Protein bands of similar size compared to those detected by the present mAbs were observed (FIGS. 3A and 3C Panel 3). The procedure was then reversed by using the known antibodies to immunoprecipitate the antigen targets and immunoblotted with TAG-1A3 and TAG-2A12 respectively. Similar results were obtained (FIGS. 3B and 3D), confirming the antigen targets of mAbs TAG-1A3 and TAG-2A12 to be ALCAM/CD166 and Prdx6 respectively. Immunostaining of the frozen cornea tissue section with anti-CD166 and anti-Prdx6 known antibodies indicated specific staining of the corneal endothelial cells, but not of stromal fibroblast cells or corneal epithelial cells (FIG. 4A), thus validating the expression of the identified antigen targets.

Figure 5:
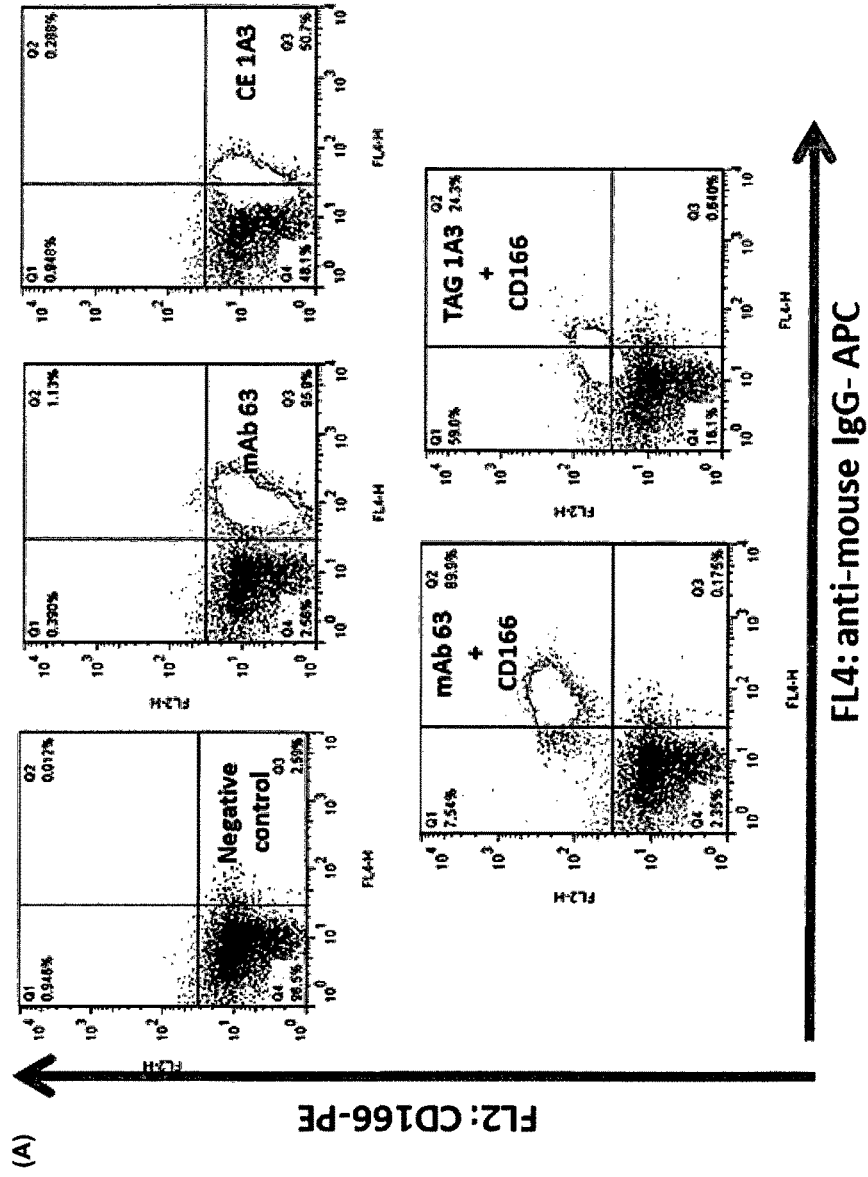
FIG. 5 shows the flow cytometry analysis plots comparing the surface binding of TAG-1A3 and TAG-2A12 against known antibodies. Section (A) shows a double staining of TAG-1A3 and CD166. mAb 63 is an in-house antibody that binds universally to human cell lines, and was used as positive control. An isotype antibody was used as a negative control. CD166, co-incubated with the positive control, did not alter the binding of CD166 (lower left panel on section A). A reduction in anti-CD166 antibody binding was observed following pre-incubation of hCENCs with TAG-1A3 but not the isotype control, mAb 63. This suggests that the antibodies were competitively binding to common epitopes on hCENC.
Figure 5:
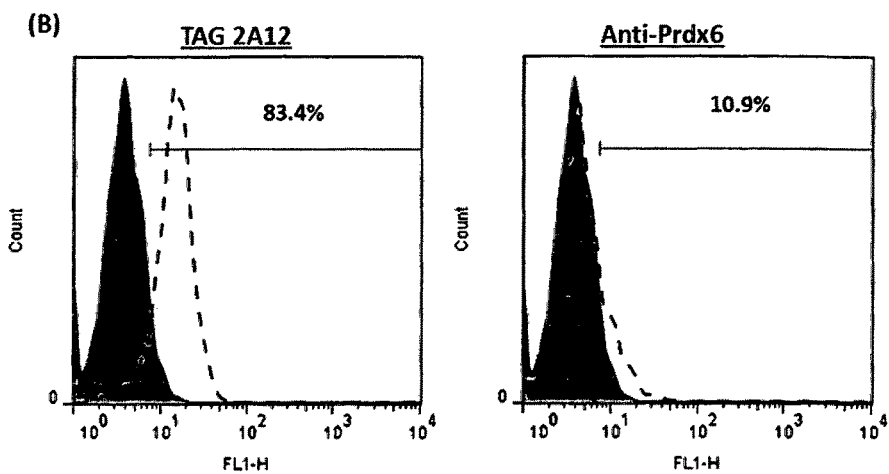
Figure 5:
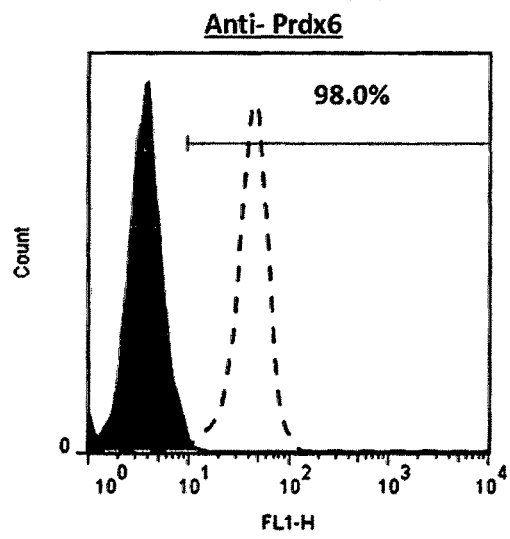

Next, cultured hCENCs were stained simultaneously using antibody pairs of a generated mAb and a known antibody, e.g. TAG-2A12 and anti-Prdx6, or TAG-1A3 and anti-CD166, and analysed using both IHC and flow cytometry to determine if these antibodies pairs were co-localizing and recognizing the same epitopes. Both TAG-1A3 and anti-CD166 antibody stained predominantly proteins located on the cell membrane or cell-to-cell junctions (FIG. 4B). By FACS, a reduction in anti-CD166 antibody binding was observed following pre-incubation of hCENCs with TAG-1A3, but not the isotype control mAb 63 (FIG. 5A). This suggests that the antibodies were competitively binding to common epitopes on hCENC. It was also shown that the anti-Prdx6 antibody only stained clusters of intracellular proteins in hCENC (FIG. 4B). Interestingly, only TAG-2A12, but not anti-Prdx6 antibody, bound to the cell surface of cultured hCENC by flow cytometry (FIG. 5B). This suggested that TAG-2A12 may be recognizing an epitope specific to cell surface-expressed Prdx6 on hCENC, whereas the known anti-Prdx6 recognizes an intracellular Prdx6.

The example above shows that the antigen target for TAG-1A3 was found to be CD166, also known as ALCAM, a protein belonging to the immunoglobulin superfamily. The function of CD166 includes development and maintenance of tissue architecture. CD166 was also detected in a wide variety of tissues; however, this was limited to only specific subsets of cells in the proliferative stages. More recently, CD166 had been implicated in many different types of cancer including lung, breast, ovarian, prostate, and colon cancers.

As for TAG-2A12, it had been determined that this mAb binds to Peroxiredoxin-6 (Prdx6). Prdx6 is sixth member of the Prdx family, albeit the only 1-cysteine member of this family; and, as opposed to using thioredoxin, utilizes glutathione as its physiological reductant. Furthermore, Prdx6 is a bi-functional protein in as much as it provides both antioxidant defence, as well as playing a role in phospholipid homeostasis. The overexpression of Prdx6 is known to increase resistance to oxidative stress, whereby it assists in reducing pre-oxidized membrane phospholipids. Furthermore, it also helps to maintain phospholipid homeostasis by regenerating the substrate metabolized by lysophospholipids. Having been first discovered in the lungs, Prdx6 was subsequently found to have a wide spread expression in many tissues of the human body. More specifically, it is known in the art that the expression of Prdx6 is associated with the eye, more particularly to lens epithelia cells (LECs). Prdx6 expression is also known in the art to negatively correlate with age and has been previously shown to gradually increase in the lens of mice from four weeks of gestation till six months after birth and decline thereafter. TAG-2A12 binds to Prdx6 expressed on the surface of hCENC. Furthermore, FIG. 9 shows the experimental results of mass spectrometric analysis of the binding of TAG-2A12 to Prdx6, whereby it was determined that the binding of TAG-2A12 to Prdx6 resulted in a sequence coverage of 20%, i.e. a sequence match of 44/224 (TAG-2A12/Prdx6 peptide).

As shown in FIG. 6D, the expression of Prdx6 varies from donor to donor. Yet, the donor-donor variations correlate very well with the morphological grading of the cells. Although the localization of Prdx6 is known to be mainly cytosolic, it had been recently suggested in the art that Prdx6 can be translocated to the plasma membrane via its interaction with p67-phox (Neutrophil cytosol factor 2). Apart from its potentially novel function in hCENC, it is believed that the expression of cell surface Prdx6 in hCENCs will serve as an ideal marker for hCENC characterization and facilitate enrichment of hCENC from complex cell mixtures.

Example 3

Quantitative Assessment of Cultured hCENC

Currently, cultured hCENC are typically characterized by their "cobblestone-like" morphology and its ZO-1 and $Na^+K^+$ ATPase markers expression. It had been previously suggested in the art that differences in both the proliferative response and the protein expression had been observed in samples from different donors. Hence, the establishment of a reliable panel of mAbs against hCENC is critical for quality assessment of these cells prior to transplantation, especially to address issues of donor to donor variations.

Samples from different donor-derived hCENC were plated and graded visually based on their morphology; "cobblestone-like" morphology was given a grade 1 and "fibroblastic-like" morphology were given a grade 3 (FIG. 6A). Expression levels of the cell surface antigens recognized by TAG-1A3 and TAG-2A12 were examined. It was found that while both mAbs were binding to cultured hCENC derived from different donors, each antibody was displaying different MFI values. More detailed analysis of the data revealed a close correlation between antigen expression of these mAbs and morphological grading (FIG. 6B), i.e. a morphological grade 1 had higher expression of TAG-2A12 than a morphological grade 3. Similar trends were observed when this data was extended to include a larger panel of donor-derived hCENCs (FIG. 6C and Table 3).

TABLE 3

Summary of multiple donor-derived hCENCs and the result of antibody binding to these samples. Listed are the respective nMFIs (normalized Mean Fluorescent Intensities) of TAG-1A3 and TAG-2A12 with its corresponding morphological grading. The sample name follows the following format: "sample_name(patient_age)pX", whereby "pX" denotes the number of sub-culturing of the tested cells.

| Sample Number (Patient Age) Passage Number Set no. | nMFI TAG 2A12 | nMFI TAG 1A3 | Morphological Grading |
|---|---|---|---|
| SN 03 (2) P3_1 | 17.66 | 12.49 | 1 |
| SN 04 (35) P2 | 10.24 | 5.59 | 1 |
| SN 01(21) P3_1 | 9.61 | 9.48 | 2 |
| SN 05 (18) P3 | 8.87 | 10.62 | 2 |
| SN 02 (18) P3_1 | 8.09 | 5.66 | 3 |
| SN 02 (18) P3_2 | 7.88 | 7.29 | 3 |
| SN 03 (18) P3_2 | 7.71 | 8.21 | 2 |
| SN 06 (23) P3_2 | 5.92 | 5.32 | 3 |
| SN 07 (26) P3 | 5.84 | 6.65 | 2 |

TABLE 3-continued

Summary of multiple donor-derived hCENCs and the result of antibody binding to these samples. Listed are the respective nMFIs (normalized Mean Fluorescent Intensities) of TAG-1A3 and TAG-2A12 with its corresponding morphological grading. The sample name follows the following format: "sample_name(patient_age)pX", whereby "pX" denotes the number of sub-culturing of the tested cells.

| Sample Number (Patient Age) Passage Number Set no. | nMFI TAG 2A12 | nMFI TAG 1A3 | Morphological Grading |
|---|---|---|---|
| SN 01 (21) P3_2 | 5.3 | 3.48 | 2 |
| SN 08 (22) P3 | 4.75 | 3.77 | 2 |
| SN 09 (26) P3_1 | 4.51 | 7.03 | 3 |
| SN 10 (34) P3 | 4.43 | 4.89 | 1 |
| SN 11 (35) P2 | 4.08 | 4.52 | 3 |
| SN 06 (23) P3_1 | 3.85 | 4.25 | 3 |
| SN 12 (32) P4 | 3.7 | 2.35 | 2 |
| SN 04 (35) P3 | 3.37 | 2.37 | 3 |
| SN 14 (19) P2 | 3.3 | 2.77 | 1 |
| SN 15 (15) P4 | 3.29 | 2.8 | 3 |
| SN 06 (23) P3_4 | 3.13 | 6.47 | 3 |
| SN 16 (22) P3 | 3.04 | 2.29 | 2 |
| SN 17 (35) P2 | 2.87 | 2.1 | 3 |
| SN 13 (33) P3 | 2.01 | 1.59 | 3 |
| SN 06 (23) P3_3 | 1.78 | 2.28 | 3 |
| SN 09 (26) P3_2 | 1.37 | 1.63 | 3 |

These results demonstrated differential trends in expression of both cell surface ALCAM/CD166 and Prdx6 in cultured hCENCs derived from various donors. Both TAG-1A3 and TAG-2A12 were highly specific for hCENCs and thus a useful tool in providing a quantitative assessment on the state of the cultured hCENC for both research and clinical applications.

Example 4

Enrichment of hCENC from Complex Cell Mixture

Tissue-engineered constructs with cultured hCENC have been known in the art to be used to treat corneal blindness. However, the requirement for isolation and expansion of the transplant grade tissues posed further challenges to the apparent limit in corneas supply. Surrogate cells, such as hPSC, have unlimited expansion and offer an alternative cell source in order to alleviate constraints due to the lack of suitable corneas. But the differentiation of hPSC is often plagued by low differentiation efficiencies and heterogeneous cell populations. The availability of human corneas proved to be one of the greatest limitations for adopting primary hCENC for transplantation. Thus, having an unlimited cell source, such as hPSC-derived hCENC, or even isolating progenitor cells during differentiation into hCENCs, remains an attractive alternative. However, because of the heterogeneity of these cell sources, efforts are required to enrich only hCENC prior to expansion for transplantation. The ability to use specific markers to enrich for hCENC in the differentiated cell population is necessary.

Figure 7:
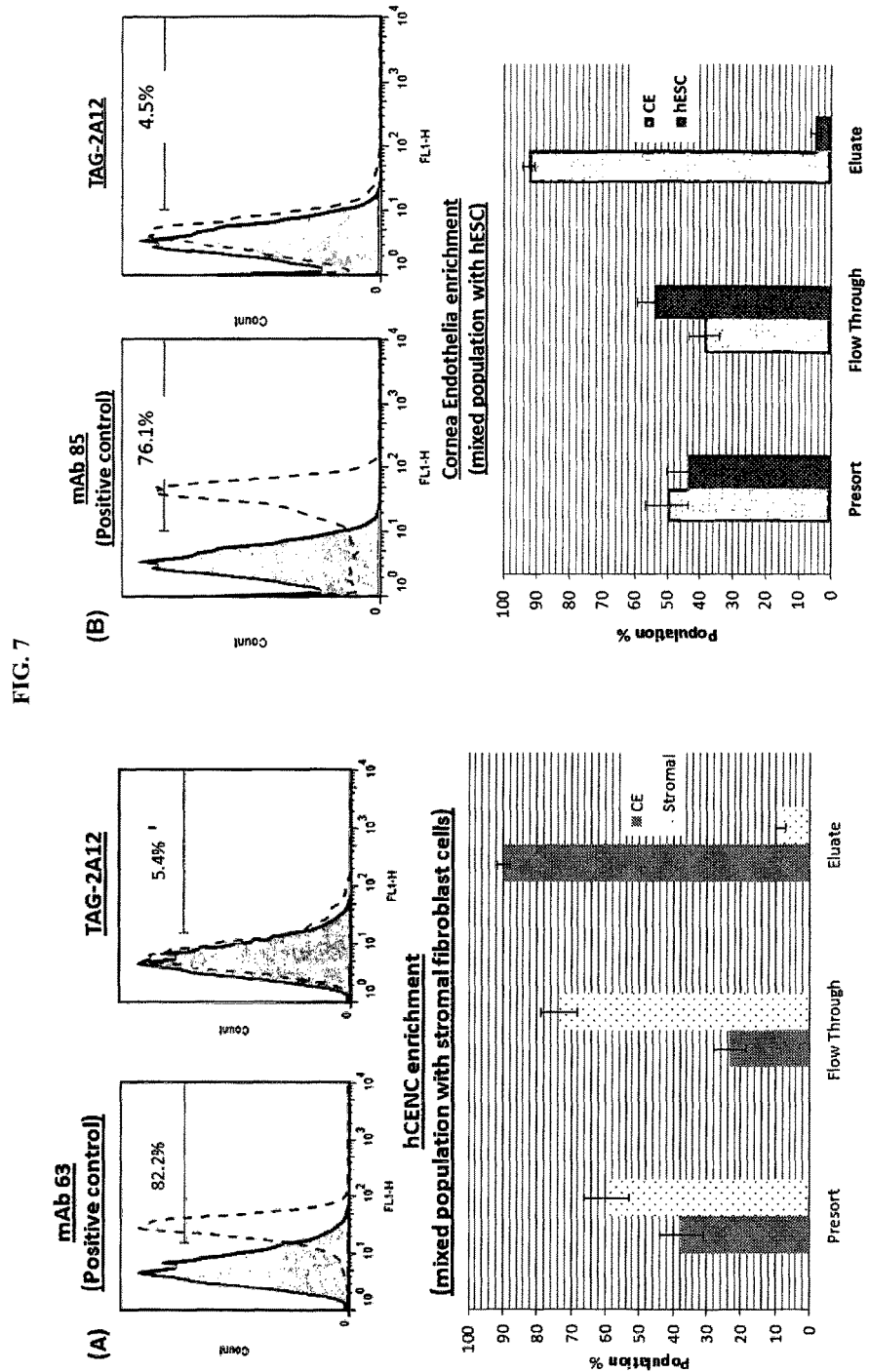
FIG. 7 shows logarithmic graphs visualising flow cytometry binding data and data showing the enrichment of hCENCs from mix cell population containing hCENCs. The enrichment was performed on a mix cell population of hCENCs with stromal fibroblast cells. Section (A) shows results of the enrichment of mix cell population of hCENCs with stromal fibroblast cells. Top panel: Flow cytometry binding data of TAG-2A12 on stromal fibroblast cells. mAb 63 was used as a positive control for stromal fibroblast cells. Bottom Panel: hCENC enrichment in 50:50 mixed population with stromal fibroblast. Enrichment of hCENCs with approximately 90% purity was achieved using MACS sorting. Experiment was conducted in triplicates. Section (B) shows the enrichment of hCENCs from a mix cell population of hCENCs with hESC (HES-3). Top panel: Flow cytometry binding data of mAb TAG-2A12 on hESC. mAb 85 was used as a positive control for hESC binding. Bottom Panel: hCENC enrichment in 50:50 mixed population with hESC. Enrichment of hCENCs with approximately 92% purity was achieved using MACS sorting. Experiment was conducted in triplicates.

TAG-2A12 was shown to bind specifically to cell-surface Prdx6 expressed on hCENC. Hence, the ability of TAG-2A12 to enrich for hCENCs non-invasively, within a mixed population of cells, was investigated. Known cell populations of either hCSF cells or undifferentiated hESCs were mixed with hCENCs as a proof-of-concept study. The cell mixture was then subjected to Magnetic-Activated-Cell-Sorting (MACS) with TAG-2A12. The negative population (hCSF or hESCs) was pre-labelled with a membrane dye before mixing with hCENCs. Both the flow-through and the eluted fractions after sorting were assessed by flow cytometry to determine relative populations in each fraction. Results from this study showed that, using a one-step immunoaffinity separation, is was possible to enrich hCENCs from a starting population of approximately 50% to ~90% purity of hCENC, in both cell mixtures with either hCSF or hESC (FIG. 7), thus proving the ability of the mAb to enrich hCENCs from heterogeneous cell samples.

As a result, TAG-2A12 was found to bind specifically to the cell surface of hCENCs, but not to hESCs or hESC-derived neural crest cells. In addition, TAG-2A12 did not bind to B4G12 cells line, an immortalized hCENC cell line (FIG. 2). This indicates that TAG-2A12 may only be present in primary hCENC, which may show a higher similarity to the corneal epithelium monolayer cells. As a proof-of-concept study, enrichment of viable hCENC was demonstrated from mixed cell populations comprising of hCENC either with hCSFs cells or hESC using MACS sorting. It had been demonstrated that the use the known antibody was possible for the enrichment of hCENCs from hCSF cells using FACS sorting. However, these had not been comprehensively panned against different cell types other than hCSF cells and cultured hCENC. Furthermore, the cell types selected for the examples were chosen to mimic a real situation that arises when hCENCs are isolated and cultivated from cadaveric or fresh donor tissue.

Surface proteins had been targets for isolation of specific cell types. It is important that changes in expression of these proteins correlate with measurable characteristics that reflect the state of the cells. The expression of cell surface CD166 and Prdx6 were monitored using TAG-1A3 and TAG-2A12, respectively, and the presented data suggested good correlation with the current standard of morphological grading of hCENC. The binding specificity of TAG-2A12 to only hCENC was exploited to help enrichment of hCENC from complex cell mixtures of either hESC or hCSF. From the data gathered, it was concluded that the mAb TAG-2A12 is a tool capable of quantitatively assessing the quality of hCENC, due to the fact that the expression of Prdx6 correlated with morphological assessment and enrichment of viable hCENC from mixed cell populations for cell transplantation.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

In addition, it is to be understood that the invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

Cell Culture

Human corneal endothelial cells and human corneal hCSFs were isolated from cornea of the cadaveric donor as previously described (Cheong et al., Invest Ophthalmol Vis Sci. 2013, 54(7): 4538-47; Chng Z et al., PLoS One. 2013, 8(7): e67546; Peh et al. BMC Res Notes. 2013, 6: 176; Peh et al., Transplantation 2011, 91(8), 811-19)). Briefly, the descement membrane (DM) and corneal endothelial cells were first peeled off from the stroma using a dissecting stereomicroscope. The DM-corneal endothelial cells were dissociated into small clumps using collagenase, followed by TrypLE Express (Life Technologies, Carlsbad, Calif., USA). Isolated hCENC were cultured on fibronectin and collagen (FnC)-coated (United States Biologicals, Swampscott, Mass., USA) tissue culture plates in F99 medium (1:1 Ham's F12 and M199) during the expansion phase, supplemented with 5% fetal bovine serum (FBS), 20 ng/ml ascorbic acid, 1× Insulin-Transferrin-Selenium, 1× antibiotic/antimycotic (AA) and 10 ng/ml of fibroblast growth factor-2 (FGF-2) The cells received fresh culture medium every other day. When hCENC reached approximately 90% confluency, the culture was replaced with a maintenance medium, which comprised endothelium, serum free medium (SFM) supplemented with 5% FBS and 1× AA, for 5 days before further sub-culturing.

The stroma button was obtained by trephination after peeling off the DM-endothelial layer as previously described (Cheong Y K et al., Invest Ophthalmol Vis Sci. 2013, 54(7): 4538-47). These cells were cultured in serum-containing medium that were changed every 2 days. Lung fibroblast cells, IMR90 were cultured in Dulbecco's modified Eagle's medium (DMEM) basal media with 10% FBS and supplemented with 2 mM L-glutamine and 1% Penicillin and Streptamycin (all from Life Technologies). The human embryonic stem cell line (hESC), HES-3, was obtained from ES Cell International (ESI BIO, Alameda, Calif., USA) and cultured on Matrigel (Becton, Dickinson and Company, Franklin Lakes, N.J., USA) with conditioned medium (CM) containing FGF-2 (Life Technologies), as described previously (Ding V M et al., J Cell Physiol. 2010, 225(2): 417-28). Cultures of H9-hESC and H9-derived neural crest cells were kindly provided by Dr Alan Colman and Dr Chng Zhen Zhi from the Institute of Molecular Biology, A*STAR Singapore.

Monoclonal Antibodies to Human Corneal Endothelial Cells

Monoclonal antibodies were raised using whole cell immunization strategy. Approximately $1 \times 10^6$ fresh cadaveric hCENC were harvested and immunized with (Sigma Adjuvant System; Sigma Aldrich Inc, Missouri, USA) into Balb-C mice for 6 consecutive weeks, followed by fusion of B cells with SP 2/O myeloma cells. Hybridomas were clonally picked after 10 to 14 days and expanded in fresh culture medium (Medium E, Stemcell Technologies, Vancouver, BC, Canada). Cell-free supernatant was collected after 7-10 days and used as primary antibodies for screening against hCENC.

Flow Cytometry

Antibodies binding to the surface of the cells were identified using flow cytometry as previously described (Choo et al., Stem Cells. 2008, 26(6): 1454-63). Normalized mean fluorescent intensity was calculated based on the MFI of sample divided by the MFI of isotype control (Chan et al., Tissue Eng Part C Methods. 2013, 19(2): 156-65). As a control for positive binding to human cell lines, an in-house derived antibody, mAb 63 was used (Choo et al.).

Immunostaining

Cornea tissues sections were prepared as previously described (Cheong et al.). The frozen sections were thawed at room temperature, followed by PBS wash before blocking with 10% goat serum (Dako, Glostrup, Denmark) for 30 min. Staining was carried out with primary antibody (supernatant) incubation for 1 h at room temperature. Alexafluor 488 and 594 conjugated rabbit anti-mouse Ig antibodies (Life Technologies), diluted to 1:500, were used as secondary antibodies. The cell nucleus was counter-stained with Vectorshield containing DAPI (Vector Laboratories, Burlingame, Calif., USA). The staining of cultured hCENC was performed with cells seeded on glass slides, which had been fixed with Reagent A (Caltag Fix and Penn Kit, An Der Grub Bio Research GmbH, Susteren, The Netherlands) for 15 mm at room temperature. Staining was carried out as described above, with either supernatant or known antibodies. The known primary antibodies used in this study were mouse IgG1 anti-ZO-1 (1:50; BD Biosciences Pharmingen, San Diego, USA), mouse IgG anti-CD166 (1:1000; Abcam, Cambridge, UK), and mouse IgG anti-Prdx6 (1:1000; Abcam). Images were taken using the Olympus light microscope IX71 fitted with a digital monochrome camera XM10 (Olympus Corporation, Japan, Tokyo).

Characterization of Antigen Target and Isotyping of TAG-1A3 and TAG-2A12

Isotyping was performed with a Mouse Monoclonal Antibody Isotyping kit from Roche (Basel, Switzerland). The protocol was carried out according to the manufacturer's instructions. Briefly, the pellet in a reaction tube was reconstituted with 150 μl of hybridoma culture supernatant from either one of the clones, TAG-1A3 or TAG-2A12. The solution was thoroughly mixed before adding the isostrip. The results were analyzed after 10 mins of incubation.

Immunoprecipitation

Total cell lysate of hCENC was prepared with 2% Triton in PBS. Immunoprecipitation (IP) was carried out using the Phynexus instrument (Phynexus Inc, USA, California), loaded with Protein G tips. The automated program allowed sequential incubation with hybridoma culture supernatant, cell lysate and washing buffer. Low pH elution was performed at the final step and the eluted sample was neutralized before use.

The samples were boiled at 95° C. after adding 5× sample loading dye and subjected to SDS-PAGE, using 4-12% gradient NuPAGE Bis-Tris gel with 1× MOPS buffer (all from Life Technologies). The proteins were separated at 100-120V for 1-2 h. The samples were prepared in duplicates, one set used for Western blot transfer onto PVDF membrane and the other for silver-staining. The membrane blot was blocked with 5% low fat milk for 30 min before incubating overnight at 4° C. with diluted culture supernatant from the primary antibody (1:3) with blocking buffer. Blots were washed with 0.1% Tween in PBS, and incubated with horseradish peroxidase (HRP) conjugated anti-mouse Ig (1:10000) at room temperature for 1 h. Finally, the blots were developed using chemiluminescence, ECL prime Western blotting detection reagent (GE Healthcare, Uppsala, Sweden). The protein band on the silver-stained gel that corresponded to the detected Western blot band was excised and digested with trypsin prior to antigen target identification using mass spectrometry (LC/MS-MS). For target validation, known antibodies anti-CD166 and anti-Prdx6 were diluted 1:100 for immunoprecipitation and 1:1000 for Western blotting.

Cell Enrichment

TAG-2A12 was used to enrich for hCENC from cell mixtures containing a 50:50 mix of either hESC or hCSF. This proof-of-concept study was performed using a positive-cell selection method with anti-mouse IgG beads from magnetic affinity cell separation (MACS; Miltenyi Biotech, Cologne Germany). The enrichment of hCENC was done following the manufacturers' protocol. Briefly, cells that constitute the negative population in the mixture (hESC or hCSFs) were first labeled with a red fluorescent cell linker PKH26 that binds to cell membrane (Sigma Aldrich Inc). The labeled cells were then added to unlabeled hCENC to obtain the starting cell mixture. After which, the cells were incubated with TAG-2A12 for 30 min at 4° C. The cells were spun down to remove unbound mAbs and washed with 1% BSA in PBS. The cell pellet was resuspended in MACS buffer and incubated with anti-mouse IgG beads for 10 min at 4° C. Cells were washed and resuspended in MACS buffer before loading onto the magnetic column. The column was subjected to several washes with MACS buffer to remove the unbound cells. Finally, bound cells were eluted in MACS buffer by removing the column from the magnetic holder and plunging the cells through the column. Flow cytometry was used to analyse the purity of the population of cells in the flow-through (FT), which contained mostly unbound cells, while the retentate contained enriched hCENC. In-house positive controls were used for fibroblast cells (mAb 63) and for hESC (mAb 85) (Choo et al., supra).

What is claimed is:

1. A monoclonal antibody that binds specifically to a human corneal endothelial cell (hCENC), wherein the target of the antibody is cell surface-expressed Peroxiredoxin-6 (Prdx6), wherein the complementarity determining regions of the antibody comprise heavy chain CDR 1 comprising SEQ ID No. 1, heavy chain CDR 2 comprising SEQ ID No. 2, heavy chain CDR 3 comprising SEQ ID No. 3, light chain CDR 1 comprising SEQ ID No. 4, light chain CDR 2 comprising SEQ ID No. 5 and light chain CDR 3 comprising SEQ ID No. 6.

2. The antibody of claim 1, wherein the antibody does not bind significantly to cells selected from the group consisting of epithelial cells, stromal fibroblast cells, human lung fibroblasts, hESC-derived neural crest cells and human embryonic stem cells.

3. The antibody according to claim 1, wherein the antibody binds to human corneal endothelial cells in a manner in which the strength of a signal derived from the binding of the antibody to the antigen is proportional to the amount of cells exhibiting a "cobblestone-like" morphology, thus enabling a grading of the human corneal endothelial cell quality.

4. The antibody according to claim 1, wherein the antibody does not bind to immortalized human corneal endothelial cells.

* * * * *